United States Patent

Tonishi et al.

Patent Number: 5,843,868
Date of Patent: Dec. 1, 1998

[54] PRYIDINE-2,3-DICARBOXYLIC ACID DIAMIDE DERIVATIVES AND HERBICIDES COMPRISING SAID DERIVATIVES AS ACTIVE INGREDIENT

[75] Inventors: Masanori Tonishi, Sakai; Takeshi Katsuhira, Kawachinagano; Takashi Ohtsuka; Yuzo Miura, both of Tondabayashi, all of Japan

[73] Assignee: Nihon Nohyaku Co., Ltd., Tokyo, Japan

[21] Appl. No.: 825,642

[22] Filed: Apr. 1, 1997

[30] Foreign Application Priority Data

Apr. 2, 1996 [JP] Japan ................... 8-104580

[51] Int. Cl.$^6$ .................. A01N 43/40; C07D 213/30
[52] U.S. Cl. ..................... 504/260; 546/316
[58] Field of Search ............... 504/260; 546/316

[56] References Cited

U.S. PATENT DOCUMENTS

| | | | |
|---|---|---|---|
| 5,262,384 | 11/1993 | Hamprecht et al. | 504/225 |
| 5,262,387 | 11/1993 | Hamprecht et al. | 504/260 |

FOREIGN PATENT DOCUMENTS

| | | |
|---|---|---|
| 0 422 456 | 4/1991 | European Pat. Off. . |
| 606843 | 7/1994 | European Pat. Off. . |
| 4213715 | 10/1993 | Germany . |
| 93/22280 | 11/1993 | WIPO . |

OTHER PUBLICATIONS

Glaznik Hem. Drustva, Beograd, "D. Dimitrijevic, ZH. TADIC: Compound of Formula V", vol. 19, pp. 33 XP000655219 (1954).

Glaznik Hem. Drustva, Beograd, "Ueber die reaktion von Chinolinimid und N–substituierten Chinolinimiden mit Aminen", Compound of Formula VIII, vol. 22, pp. 473–481, XP002034365 (1957).

*Primary Examiner*—Jane Fan
*Attorney, Agent, or Firm*—Cushman Darby & Cushman IP Group of Pillsbury Madison & Sutro LLP

[57] ABSTRACT

The present invention provides a pyridine-2,3-dicarboxylic acid diamide derivatives represented by the following formula (I) and herbicides containing them as an active ingredient.

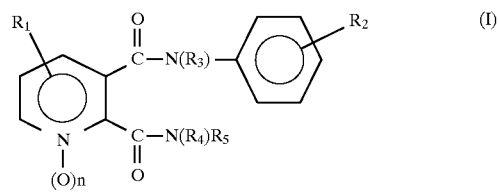

[wherein $R_1$ represents one to three substituents such as H, halogen, cyano, nitro, (halo)alkyl, (halo)alkoxy, (halo)alkylthio, $(C_{3-6})$cycloalkyl, alkenyl, alkynyl, substituted phenyl, substituted phenoxy, etc. and $R_1$ may represent alkylene or alkenylene together with an adjacent carbon atom; $R_2$ represents H, halogen, cyano, nitro, (halo)alkyl or (halo)alkoxy; $R_3$ represents H or alkyl; $R_4$ and $R_5$ each represent H, (halo)alkyl, cycloalkyl, substituted cycloalkylalkyl, etc.; and n represents an integer of 0 or 1].

The present compounds exhibit excellent effect for controlling paddy field weeds and the like.

4 Claims, No Drawings

PRYIDINE-2,3-DICARBOXYLIC ACID DIAMIDE DERIVATIVES AND HERBICIDES COMPRISING SAID DERIVATIVES AS ACTIVE INGREDIENT

BACKGROUND OF THE INVENTION

1. Field of the Invention

The present invention relates to a novel pyridine-2,3-dicarboxylic acid diamide derivative and a herbicide comprising the compound as an active ingredient.

2. Related Art

DE4213715-A1, WO93/22280-A1 and EP606843-A1 disclose compounds similar to the pyridine-2,3-dicarboxylic acid diamide derivative of the present invention as herbicides or plant growth regulators.

SUMMARY OF THE INVENTION

As a result of intensive research conducted by the inventors in an attempt to develop novel herbicides, it has been found that pyridine-2,3-dicarboxylic acid diamide derivatives represented by the formula (I) are novel compounds which have never been disclosed in literatures and have markedly higher herbicidal activities than those of compounds disclosed in the prior art. Thus, the present invention has been accomplished.

DETAILED DESCRIPTION OF THE INVENTION

The present invention relates to pyridine-2,3-dicarboxylic acid diamide derivatives represented by the following formula (I) and herbicides containing these compounds:

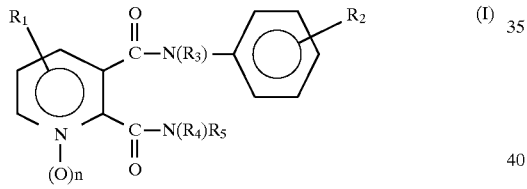

[wherein $R^1$ represents one to three substituents which may be the same or different and are selected from the group consisting of a hydrogen atom; a halogen atom; a cyano group; a nitro group; a $(C_{1-6})$alkyl group; a halo-$(C_{1-6})$alkyl group; a $(C_{1-6})$alkoxy group; a halo$(C_{1-6})$alkoxy group; a $(C_{1-6})$alkylthio group; a halo$(C_{1-6})$alkylthio group; a $(C_{1-6})$alkylsulfinyl group; a halo$(C_{1-6})$alkylsulfinyl group; a $(C_{1-6})$alkylsulfonyl group; a halo$(C_{1-6})$alkylsulfonyl group; a $(C_{3-6})$ cycloalkyl group; a $(C_{2-6})$-alkenyl group; a $(C_{2-6})$ alkynyl group; a $(C_{1-6})$alkoxy-$(C_{1-6})$alkyl group; a phenyl group; a substituted phenyl group having one or more substituents which may be the same or different and are selected from the group consisting of a halogen atom, a $(C_{1-6})$alkyl group, a halo$(C_{1-6})$alkyl group, a $(C_{1-6})$alkoxy group, a halo-$(C_{1-6})$alkoxy group, a $(C_{1-6})$alkylthio group and a halo$(C_{1-6})$alkylthio group; a phenoxy group; a substituted phenoxy group having one or more substituents which may be the same or different and are selected from the group consisting of a halogen atom, a $(C_{1-6})$alkyl group, a halo $(C_{1-6})$alkyl group, a $(C_{1-6})$alkoxy group, a halo$(C_{1-6})$-alkoxy group, a $(C_{1-6})$alkylthio group and a halo$(C_{1-6})$-alkylthio group; a phenylthio group; a substituted phenylthio group having one or more substituents which may be the same or different and are selected from the group consisting of a halogen atom, a $(C_{1-6})$alkyl group, a halo$(C_{1-6})$alkyl group, a $(C_{1-6})$alkoxy group, a halo$(C_{1-6})$alkoxy group, a $(C_{1-6})$ alkylthio group and a halo$(C_{1-6})$alkylthio group; and an amino group substituted with a hydrogen atom or a $(C_{1-6})$ alkyl group which may be the same or different, and $R_1$ may represent a $(C_{3-4})$alkylene group or a $(C_{3-4})$alkenylene group together with an adjacent carbon atom, $R_2$ represents one to five substituents which may be the same or different and are selected from the group consisting of a hydrogen atom, a halogen atom, a cyano group, a nitro group, a $(C_{1-6})$alkyl group, a halo-$(C_{1-6})$ alkyl group, a $(C_{1-6})$alkoxy group, a halo$(C_{1-6})$alkoxy group, a $(C_{1-6})$alkoxycarbonyl group and a $(C_{1-6})$ alkoxy-carbonyl$(C_{1-6})$alkyloxy group, $R_3$ represents a hydrogen atom or a $(C_{1-6})$alkyl group, $R_4$ and $R_5$ may be the same or different and each represent a hydrogen atom; a $(C_{1-6})$alkyl group; a halo-$(C_{1-6})$ alkyl group; a cyano$(C_{1-6})$alkyl group; a $(C_{3-6})$ cycloalkyl group; a $(C_{3-6})$cycloalkyl$(C_{1-6})$alkyl group; a $(C_{3-6})$-cycloalkyl$(C_{1-6})$alkyl group having one or more halogen atoms on the ring which may be the same or different; a $(C_{1-6})$alkoxy$(C_{1-6})$alkyl group; a $(C_{1-6})$ alkylthio$(C_{1-6})$alkyl group; a $(C_{1-6})$alkoxycarbonyl $(C_{1-6})$ alkyl group; a $(C_{2-6})$-alkenyl group; a $(C_{2-6})$ alkynyl group; a phenyl$(C_{1-6})$alkyl group, an amino group substituted with a halogen atom or a $(C_{1-6})$alkyl group which may be same or different; an amino$(C_{1-6})$ alkyl group substituted with a hydrogen atom or a $(C_{1-6})$alkyl group which may be the same or different; a phenyl$(C_{1-6})$alkyloxy group or a 5–6 membered heterocyclic-$(C_{1-6})$alkyl group having one or more hetero-atoms which may be the same or different and are selected from the group consisting of an oxygen atom, a sulfur atom and a nitrogen atom, and the carbon atom or nitrogen atom on the ring of the heterocyclic-$(C_{1-6})$alkyl group may have one or more substituents which may be the same or different and are selected from the group consisting of a halogen atom, a $(C_{1-6})$ alkyl group, a halo$(C_{1-6})$alkyl group, a $(C_{1-6})$alkoxy group, a halo$(C_{1-6})$-alkoxy group, a $(C_{1-6})$alkylthio group, a halo$(C_{1-6})$-alkylthio group and a phenyl$(C_{1-6})$ alkyl group, and $R_4$ and $R_5$ together may represent a 5–6 membered heterocyclic ring having one or more hetero-atoms which may be the same or different and are selected from the group consisting of an oxygen atom, a sulfur atom and a nitrogen atom, and the carbon atom or nitrogen atom on the heterocyclic ring may have one or more substituents which may be the same or different and are selected from the group consisting of a halogen atom, a $(C_{1-6})$alkyl group, a halo$(C_{1-6})$ alkyl group, a $(C_{1-6})$alkoxy group, a halo$(C_{1-6})$alkoxy group, a $(C_{1-6})$alkylthio group and a halo$(C_{1-6})$ alkylthio group; and n represents an integer of 0 or 1].

As to definitions in the formula (I) of the pyridine-2,3-dicarboxylic acid diamide derivative of the present invention, "halogen atom" means a chlorine atom, a bromine atom, an iodine atom or a fluorine atom, "$(C_{1-6})$alkyl group" means a straight chain or branched chain alkyl group of 1–6 carbon atoms, such as methyl, ethyl, n-propyl, i-propyl, n-butyl, i-butyl, s-butyl, t-butyl, n-pentyl, n-hexyl or the like, and "halo$(C_{1-6})$-alkyl group" means a straight chain or branched chain alkyl group of 1–6 carbon atoms substituted with one or more halogen atoms which may be the same or different.

Preferable examples of substituent for $R_1$ are a halogen atom, such as chlorine, bromine, fluorine or iodine, a $(C_{1-3})$ alkyl group such as methyl, ethyl, n-propyl or i-propyl, a $(C_{1-3})$alkylthio group such as ethylthio, ethylthio, n-propylthio or i-propylthio, a $(C_{1-3})$alkylsulfonyl group such as methylsulfonyl, ethylsulfonyl, n-propylsulfonyl or i-propylsulfonyl, a $(C_{3-4})$alkenyl group such as propenyl or butenyl.

Preferable examples of substituent for $R_2$ are a halogen atom, such as chlorine, bromine, fluorine or iodine or a $(C_{1-3})$alkyl group such as methyl, ethyl, n-propyl or i-propyl.

Preferable examples of substituent for $R_3$ is a hydrogen atom.

Preferable examples of substituent for $R_4$ and $R_5$ are a $(C_{1-3})$alkyl group such as methyl, ethyl, n-propyl or i-propyl or a cyclo$(C_{3-6})$alkyl group such as cyclo-propyl, cyclo-butyl, cyclo-pentyl or cyclo-hexyl.

The pyridine-2,3-dicarboxylic acid diamide derivatives of the present invention represented by the formula (I) can be prepared, for example, by the processes illustrated below.

2,3-dicarboxylic acid diamide derivative represented by the formula (I-1) can be produced.

A-1. Formula (IV-1) or (IV-2)→Formula (III):

The inert solvents usable in this reaction can be any inert solvents as long as they do not significantly hinder the progress of the reaction, and they can be exemplified by halogenated hydrocarbons such as dichloromethane, chloroform, carbon tetrachloride and the like; aromatic hydrocarbons such as benzene, toluene, xylene, chlorobenzene and the like; chain or cyclic ethers such as methyl cellosolve, diethyl ether, diisopropyl ether, dioxane, tetrahydrofuran and the like; and organic acids such as acetic acid, trifluoroacetic acid and the like. These inert solvents may be used each alone or in admixture.

Furthermore, the dehydrating agent can be used in excess in place of the inert solvent.

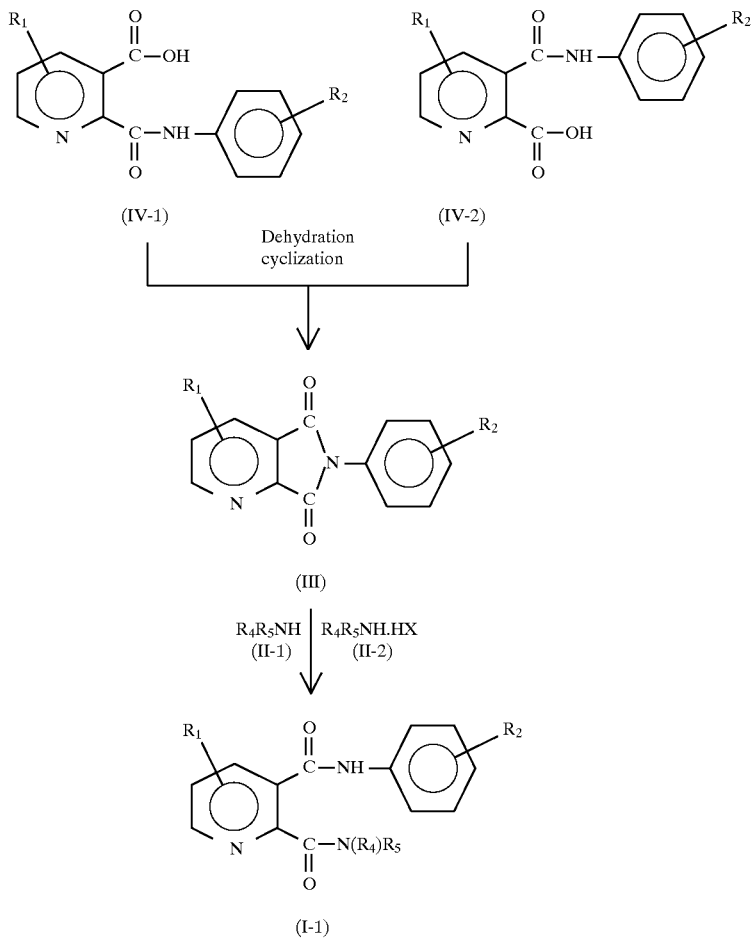

Process A (wherein $R_1$, $R_2$, $R_4$ and $R_5$ are as defined above, and X represents a halogen atom).

A compound represented by the formula (IV-1) or (IV-2) is subjected to cyclization reaction with a dehydrating agent in the presence or absence of an inert solvent to yield an imide represented by the formula (III). The imide is, after isolation or without isolation, reacted with an amine or a salt thereof represented by the formula (II-1) or (II-2) in the presence or absence of an inert solvent and in the presence or absence of an inert solvent of a base, whereby a pyridine- The dehydrating agent includes, for example, acetic anhydride, trifluoroacetic anhydride and the like. The amount of the dehydrating agent can be appropriately selected from the range of one to more moles for 1 mole of the compound represented by the formula (IV-1) or (IV-2). Preferably, it is used in an equimolar amount.

The reaction temperature can be appropriately selected from the range of room temperature to the boiling point of the inert solvent used. In the case of using no inert solvent, the reaction may be carried out at the boiling point of the dehydrating agent.

The reaction time may vary depending on the reaction temperature, reaction scale or the like, but can be in the range of several minutes to 48 hours.

After completion of the reaction, the intended product is isolated from the reaction mixture containing it by conventional method and, if necessary, purified by recrystallization, distillation, column chromatography and the like, whereby the intended product can be produced.

After completion of the reaction, the product can be used for the subsequent reaction, as it is, without isolation.

A-2. Formula (III)→Formula (I-1):

Inert solvents usable in this reaction include pyridyls in addition to those exemplified in the above A-1.

Since the present reaction is an equimolar reaction, an amine represented by the formula (II-1) or a salt thereof represented by the formula (II-2) may be used in an amount of one mole per one mole of the compound represented by the formula (III). However, it can be used in excess.

When the salt of amine represented by the formula (II-2) is used in the present reaction, a base is required to produce a free amine in the reaction system. The base is an inorganic base or an organic base. The inorganic bases include, for example, hydroxides and carbonates of alkali metal atoms, such as sodium hydroxide, potassium hydroxide, sodium carbonate, and potassium carbonate, and organic bases include, for example, triethylamine, pyridine, 4-dimethylamino-pyridine and 1,8-diazabicyclo[5,4,0]-7-undecene. The amount of the bases can be appropriately selected from the range of one to more moles per one mole of the salt of amine represented by the formula (II-2). The reaction temperature can be appropriately selected from the range of $-10°$ C. to the boiling point of the inert solvent used and is preferably in the range of $0°–150°$ C.

The reaction time depends on the reaction temperature, reaction scale or the like, but can be in the range of several minutes to 48 hours.

After completion of the reaction, the intended product is isolated from the reaction mixture containing it by conventional method and, if necessary, purified by recrystallization, distillation, column chromatography and the like, whereby the intended product can be produced.

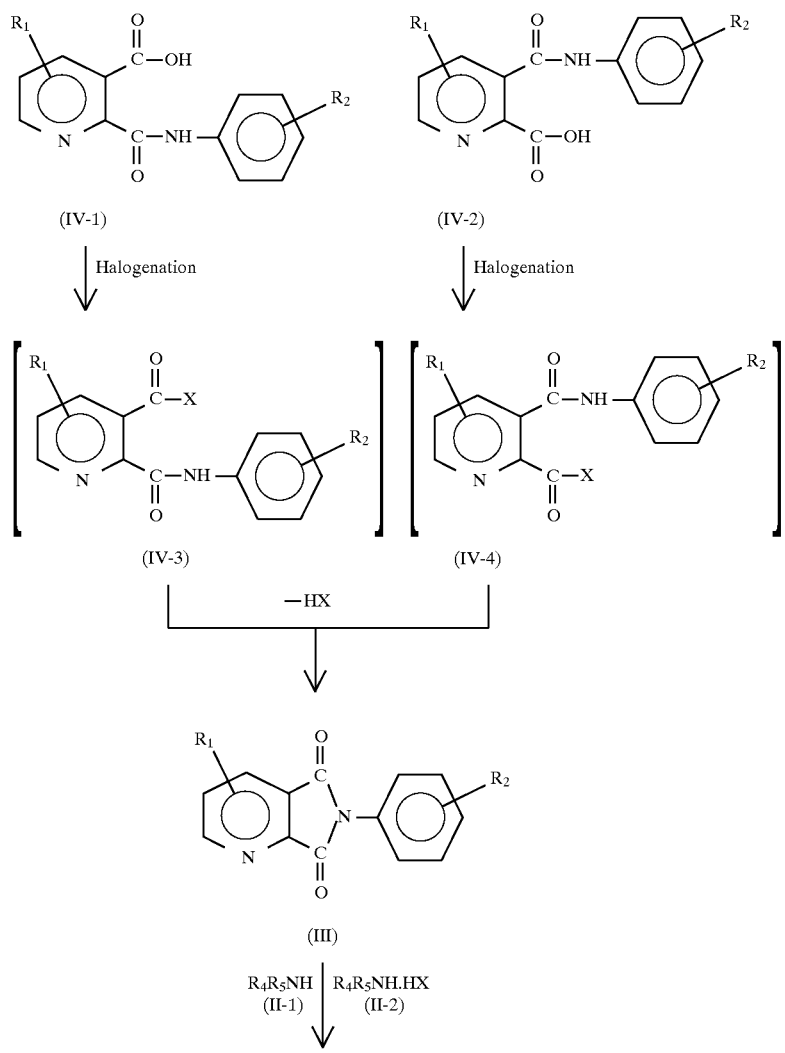

Process B.

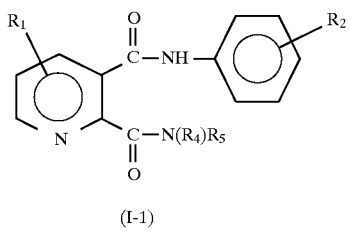

(I-1)

(wherein $R_1$, $R_2$, $R_4$, $R_5$ and X are as defined above).

A compound represented by the formula (IV-1) or (IV-2) is reacted with a halogenating agent in the presence or absence of an inert solvent to yield an acid halide represented by the formula (IV-3) or (IV-4). A cyclization reaction of the acid halide which is not isolated proceeds in the reaction system with releasing a hydrogen halide to yield an imide represented by the formula (III). The imide is, after isolation or without isolation, reacted with an amine or a salt thereof represented by the formula (II-1) or (II-2) in the presence or absence of an inert solvent and in the presence or absence of an inert solvent of a base, whereby a pyridine-2,3-dicarboxylic acid diamide derivative represented by the formula (I-1) can be produced.

B-1. Formula (IV-1)→[Formula (IV-3)]→Formula (III) or Formula (IV-2)→[Formula (IV-4)]→Formula (III):

Inert solvents usable in this reaction include, for example, those exemplified in the above A-1 and, in addition, the halogenating agent can be used in excess as the inert solvent.

Examples of the halogenating agent are oxalyl chloride, thionyl chloride, phosphorus trichloride, phosphorus pentachloride, thionyl bromide, phosphorus tribromide and the like. The amount of the halogenating agent used can be selected from the range of one to more moles per mole of the compound represented by the formula (IV-1) or (IV-2), and is preferably in excess.

A catalytic amount of iodine, zinc chloride, pyridine, triethylamine, dimethylformamide, hexaphosphoric triamide, 4-dimethylaminopyridine, N,N'-tetramethylurea and the like can be added for the acceleration of the reaction.

The reaction temperature can be appropriately selected from the range of room temperature to the boiling point of the inert solvent used and is preferably in the range of 20°–150° C.

The reaction time depends on the reaction temperature, reaction scale or the like, but can be in the range of several minutes to 48 hours.

After completion of the reaction, the intended product is isolated from the reaction mixture containing it by conventional method and, if necessary, purified by recrystallization, distillation, column chromatography and the like, whereby the intended product can be produced.

B-2. Formula (III)→Formula (I-1):

This reaction can be carried out according to the procedure of A-2.

Process C.

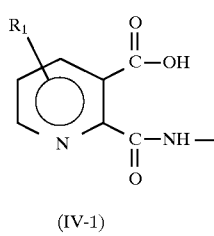 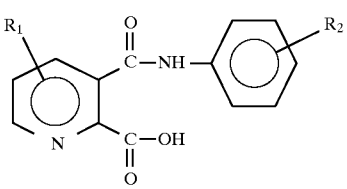

(IV-1)    (IV-2)

↓ $R_5$—OH (V)    ↓ $R_6$—OH (V)

Process C.

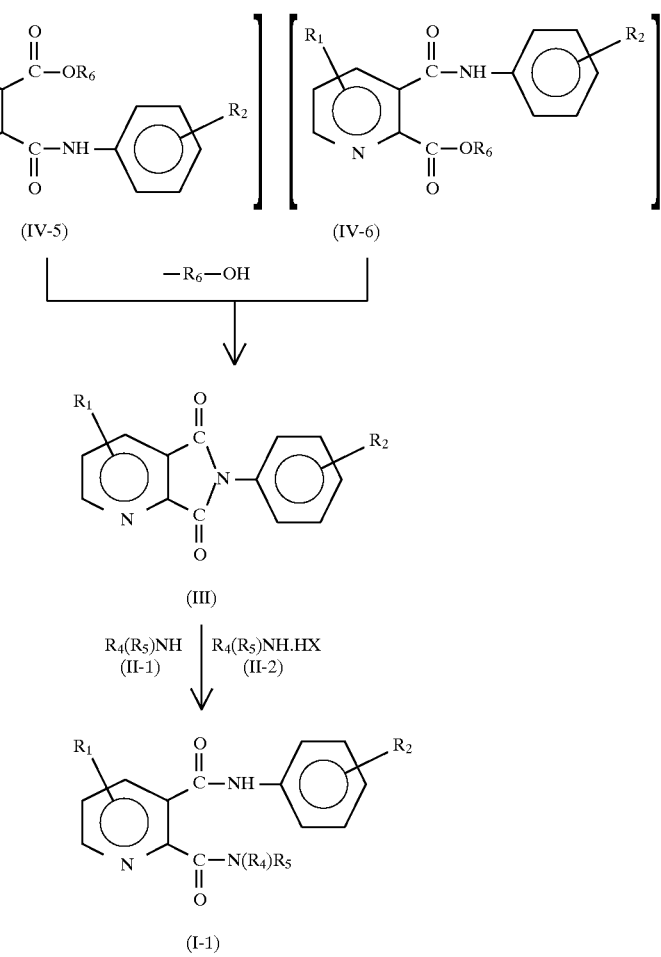

(wherein $R_1$, $R_2$, $R_4$, $R_5$ and X are as defined above, and $R_6$ is a ($C_{1-6}$)alkyl group).

A compound represented by the formula (IV-1) or (IV-2) and an alcohol represented by the formula (V) are subjected to an esterification reaction in the presence of an inert solvent and in the presence of a dehydrating agent such as sulfuric acid or p-toluenesulfonic acid to yield an ester represented by the formula (IV-5) or (IV-6). A cyclization reaction of the ester which is not isolated proceeds in the reaction system with releasing an alcohol to yield an imide represented by the formula (III). The imide is, after isolation or without isolation, reacted with an amine or a salt thereof represented by the formula (II-1) or (II-2) in the presence or absence of an inert solvent and in the presence or absence of an inert solvent of a base, whereby a pyridine-2,3-dicarboxylic acid diamide derivative represented by the formula (I-1) can be produced.

C-1. Formula (IV-1)→[Formula (IV-5)]→Formula (III) or Formula (IV-2)→[Formula (IV-6)]→Formula (III):

Inert solvents usable in this reaction include, for example, those exemplified in the above A-1 and, in addition, the alcohol represented by the formula (V) can be used in an excess amount as the inert solvent.

The amount of the dehydrating agent such as sulfuric acid, p-toluenesulfonic acid or the like can be selected from the range of one to more moles per mole of the compound represented by the formula (IV-1) or (IV-2).

The reaction temperature can be appropriately selected from the range of room temperature to the boiling point of the inert solvent used and is preferably in the range of 20°–150° C.

The reaction time depends on the reaction temperature, reaction scale or the like, but can be in the range of several minutes to 48 hours.

After completion of the reaction, the intended product is isolated from the reaction mixture containing it by conventional method and, if necessary, purified by recrystallization, distillation, column chromatography and the like, whereby the intended product can be produced.

C-2. Formula (III)→Formula (I-1):

This reaction can be carried out according to the procedure of A-2.

Process D.

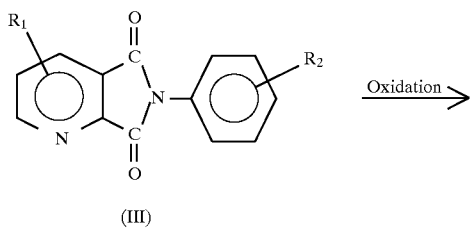

Process D.

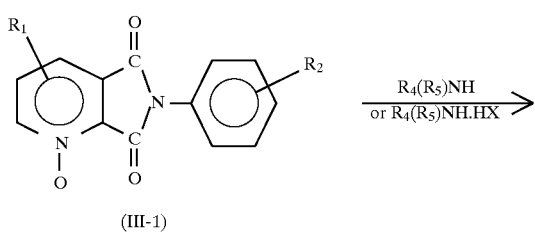

(III-1)

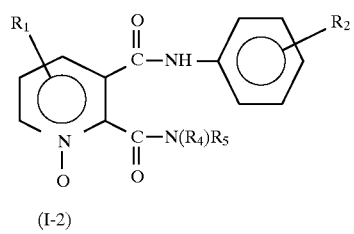

(I-2)

(wherein $R_1$, $R_2$, $R_4$, $R_5$ and X are as defined above).

An imide represented by the formula (III) is subjected to oxidation reaction with an oxidizing agent in the presence of an inert solvent to yield an imide oxidation product. The imide oxidation product is, after isolation or without isolation, reacted with an amine or a salt thereof represented by the formula (II-1) or (II-2) in the presence or absence of an inert solvent and in the presence or absence of an inert solvent of a base, whereby a pyridine-2,3-dicarboxylic acid diamide derivative represented by the formula (I-2) can be produced.

D-1. Formula (III)→Formula (III-1):

Inert solvents usable in this reaction include, for example, halogenated hydrocarbons such as dichloromethane, chloroform, carbon tetrachloride and the like and aromatic hydrocarbons such as benzene, toluene, xylene, chlorobenzene and the like. These inert solvents can be used each alone or in admixture.

The oxidizing agents usable are organic peracids, such as peracetic acid, m-perchlorobenzoic acid and the like. The amount of the oxidizing agent can be selected from the range of one to more moles per mole of the imide represented by the formula (III).

The reaction temperature can be appropriately selected from the range of room temperature to the boiling point of the inert solvent used and is preferably in the range of the boiling point of the inert solvent.

The reaction time depends on the reaction temperature, reaction scale or the like, but can be in the range of several minutes to 48 hours.

After completion of the reaction, the intended product can be produced in the same manner as in A-1.

D-2. Formula (III-1)→Formula (I-2):

This reaction can be carried out according to the procedure of A-2 to produce the intended product.

Process E.

(III-2)

(III-3)

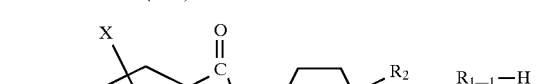

(III-4)

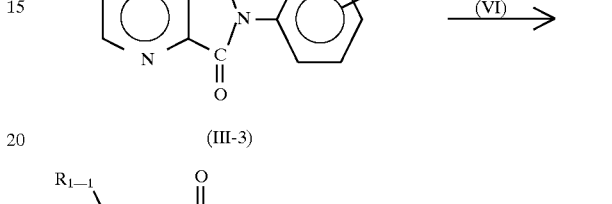

(I-3)

(wherein $R_1$, $R_2$, $R_4$, $R_5$ and X are as defined above, and $R_{1-1}$ represents a phenylthio group or a phenylthio group having one or more substituents which may be the same or different and are selected from the group consisting of a halogen atom, a ($C_{1-6}$)alkyl group, a halo($C_{1-6}$)alkyl group, a ($C_{1-6}$) alkoxy group, a halo($C_{1-6}$)alkoxy group, a ($C_{1-6}$)alkylthio group and a halo($C_{1-6}$)alkylthio group).

An imide represented by the formula (III) is subjected to halogenation reaction with a halogenating agent in the presence or absence of an inert solvent to yield an imide represented by the formula (III-3). The imide is, after isolation or without isolation, reacted with a compound represented by the formula (VI) in the presence or absence of an inert solvent and in the presence or absence of a base to yield an imide represented by the formula (III-4). This imide is, after isolation or without isolation, reacted with an amine or a salt thereof represented by the formula (II-1) or (II-2) in the presence or absence of an inert solvent and in the presence or absence of an inert solvent of a base, whereby a pyridine-2,3-dicarboxylic acid diamide derivative represented by the formula (I-3) can be produced.

E-1. Formula (III-2)→Formula (III-3):

This reaction can be carried out in accordance with the procedure described in EPC Laid-Open Application 0422456A2 or JP-A-3-133982 to produce the intended product.

E-2. Formula (III-3)→Formula (III-4):

Examples of the inert solvent used in this reaction are halogenated hydrocarbons such as methylene chloride, chloroform, carbon tetrachloride and the like; aromatic hydrocarbons such as benzene, toluene, xylene and the like; esters such as ethyl acetate and the like; nitrites such as acetonitrile, benzonitrile and the like; chain or cyclic ethers such as methyl cellosolve, diethyl ether, dioxane, tetrahydrofuran and the like; sulfolane; dimethyl sulfoxide; dimethyl sulfone; and water. These inert solvents can be used each alone or in admixture. When a two phase type mixed solvent comprising water and an organic solvent is used, it is possible to use a phase transfer catalyst such as trimethylbenzylammonium chloride or the like together with a base.

The base usable in the present invention is an inorganic base or an organic base. The inorganic base includes, for example, hydroxides, carbonates or alcohorates of alkali metals or alkaline earth metals such as sodium, potassium, magnesium and calcium. The organic base includes, for example, triethylamine, pyridine and the like. The amount of the base can be appropriately selected from the range of one to more moles per mole of the imide represented by the formula (III-3).

Since this reaction is an equimolar reaction, the imide represented by the formula (III-3) and the compound represented by the formula (VI) may be used in equimolar amounts, but one of them can be used in excess.

The reaction temperature can be appropriately selected from the range of room temperature to the boiling point of the inert solvent used.

The reaction time depends on the reaction temperature, reaction scale or the like, but can be in the range of several minutes to 48 hours.

After completion of the reaction, the intended product can be isolated by conventional method.

E-3. Formula (III-4)→Formula (I-3):

This reaction can be effected according to A-2 to produce the intended product.

Typical examples of pyridine-2,3-dicarboxylic acid diamide derivatives represented by the formula (I) are shown in Table 1. However, these examples are never limiting the present invention.

TABLE 1

(R3 is hydrogen atom and n is 0.)

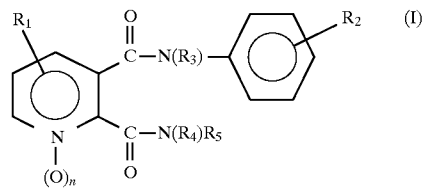

| No. | $R_1$ | $R_2$ | $R_4$ | $R_5$ | Melting point or refractive index |
|---|---|---|---|---|---|
| 1 | H | 2,5-$Cl_2$ | H | i-$C_4H_9$ | 132.6° C. |
| 2 | H | 2,5-$Cl_2$ | H | c-$C_5H_9$ | 172.0° C. |
| 3 | H | 2,4-$F_2$ | H | i-$C_3H_7$ | 201.1° C. |
| 4 | H | 2,4-$F_2$ | H | i-$C_4H_9$ | 241.0° C. |
| 5 | H | 2,6-$F_2$ | H | n-$C_3H_7$ | 159.8° C. |
| 6 | H | 2,6-$F_2$ | H | i-$C_3H_7$ | 162.3° C. |
| 7 | H | 2,6-$F_2$ | H | i-$C_4H_9$ | 180.6° C. |
| 8 | H | 2-$CH_3$-3-Cl | H | H | 205° C. |
| 9 | H | 2-$CH_3$-3-Cl | H | $CH_3$ | 175–176° C. |
| 10 | H | 2-$CH_3$-3-Cl | H | $C_2H_5$ | 163–164° C. |
| 11 | H | 2-$CH_3$-3-Cl | H | n-$C_3H_7$ | 153.5–154.5° C. |
| 12 | H | 2-$CH_3$-3-Cl | H | n-$C_3H_7$ | 187–188° C. Pyridine N-oxide |
| 13 | H | 2-$CH_3$-3-Cl | H | i-$C_3H_7$ | 205° C. |
| 14 | H | 2-$CH_3$-3-Cl | H | n-$C_4H_9$ | 143–144° C. |
| 15 | H | 2-$CH_3$-3-Cl | H | i-$C_4H_9$ | 131–132° C. |
| 16 | H | 2-$CH_3$-3-Cl | H | i-$C_4H_9$ | 187–189° C. Pyridine N-oxide |
| 17 | H | 2-$CH_3$-3-Cl | H | s-$C_4H_9$ | 160.5° C. |
| 18 | H | 2-$CH_3$-3-Cl | H | t-$C_4H_9$ | 166–167° C. |
| 19 | H | 2-$CH_3$-3-Cl | H | n-$C_5H_{11}$ | 124° C. |
| 20 | H | 2-$CH_3$-3-Cl | H | i-$C_5H_{11}$ | 146–147° C. |
| 21 | H | 2-$CH_3$-3-Cl | H | $CH(CH_3)C_3H_7$ | 133° C. |
| 22 | H | 2-$CH_3$-3-Cl | H | $CH_2CH(CH_3)C_2H_5$ | 122–124° C. |
| 23 | H | 2-$CH_3$-3-Cl | H | $CH(CH_3)CH(CH_3)_2$ | 144° C. |
| 24 | H | 2-$CH_3$-3-Cl | H | $CH_2C(CH_3)_3$ | 163–164° C. |
| 25 | H | 2-$CH_3$-3-Cl | H | $CH(C_2H_5)_2$ | 144° C. |
| 26 | H | 2-$CH_3$-3-Cl | H | n-$C_6H_{11}$ | 138° C. |
| 27 | H | 2-$CH_3$-3-Cl | H | $CH(CH_3)CH_2CH(CH_3)_2$ | nD 1.5712(20.0° C.) |
| 28 | H | 2-$CH_3$-3-Cl | H | $CH_2CH_2Cl$ | 157° C. |
| 29 | H | 2-$CH_3$-3-Cl | H | $CH_2CH_2F$ | 164–165° C. |
| 30 | H | 2-$CH_3$-3-Cl | H | $CH_2CH_2CH_2Br$ | 138–140° C. |
| 31 | H | 2-$CH_3$-3-Cl | H | $CH_2CH_2CH_2Cl$ | 151–152° C. |
| 32 | H | 2-$CH_3$-3-Cl | H | c-$C_3H_7$ | 165–167° C. |
| 33 | H | 2-$CH_3$-3-Cl | H | c-$C_5H_9$ | 163–164° C. |
| 34 | H | 2-$CH_3$-3-Cl | H | c-$C_6H_{11}$ | 188° C. |

TABLE 1-continued (R3 is hydrogen atom and n is 0.)

$$\text{(I)}$$

Structure: Pyridine ring with $R_1$ substituent, $C(=O)-N(R_3)$-phenyl-$R_2$ group, $C(=O)-N(R_4)R_5$ group, and $(O)_n$ on nitrogen.

| No. | $R_1$ | $R_2$ | $R_4$ | $R_5$ | Melting point or refractive index |
|---|---|---|---|---|---|
| 35 | H | 2-CH$_3$-3-Cl | H | CH$_2$CH=CH$_2$ | 162–163° C. |
| 36 | H | 2-CH$_3$-3-Cl | H | CH$_2$C(CH$_3$)=CH$_2$ | 158.5–159° C. |
| 37 | H | 2-CH$_3$-3-Cl | H | CH$_2$C≡CH | 187° C. |
| 38 | H | 2-CH$_3$-3-Cl | H | CH$_2$CH$_2$OCH$_3$ | 159–160° C. |
| 39 | H | 2-CH$_3$-3-Cl | H | (CH$_2$)$_3$OCH$_3$ | 106–110° C. |
| 40 | H | 2-CH$_3$-3-Cl | H | CH$_2$CH$_2$CN | 186.5–188.6° C. |
| 41 | H | 2-CH$_3$-3-Cl | H | (CH$_2$)$_3$CO—OC$_2$H$_5$ | 125–127° C. |
| 42 | H | 2-CH$_3$-3-Cl | H | CH$_2$-c-C$_3$H$_5$ | 159–160° C. |
| 43 | H | 2-CH$_3$-3-Cl | CH$_3$ | i-C$_4$H$_9$ | 128–137° C. |
| 44 | H | 2-CH$_3$-3-Cl | H | CH$_2$-Ph | 174.5–175.0° C. |
| 45 | H | 2-CH$_3$-3-Cl | H | CH(CH$_3$)-Ph | 167° C. |
| 46 | H | 2-CH$_3$-3-Cl | H | CH$_2$CH$_2$-Ph | 171–172° C. |
| 47 | H | 2-CH$_3$-3-Cl | H | OCH$_2$-Ph | 164° C. |
| 48 | H | 2-CH$_3$-3-Cl | H | CH$_2$CH$_2$N(CH$_3$)$_2$ | 113–115° C. |
| 49 | H | 2-CH$_3$-3-Cl | H | CH$_2$-Fury | 126–128° C. |
| 50 | H | 2-CH$_3$-3-Cl | \multicolumn{2}{l}{—(CH$_2$)$_4$—} | 142–143° C. |
| 51 | H | 2-CH$_3$-3-Cl | \multicolumn{2}{l}{—(CH$_2$)$_5$—} | 159° C. |
| 52 | H | 2-CH$_3$-3-Cl | \multicolumn{2}{l}{—(CH$_2$)$_2$—O—(CH$_2$)$_2$—} | 181° C. |
| 53 | H | 2-CH$_3$-3-Cl | \multicolumn{2}{l}{—(CH$_2$)$_2$—N(CH$_3$)—(CH$_2$)$_2$—} | 158° C. |
| 54 | H | 2-CH$_3$-5-Cl | H | CH$_3$ | 158.2° C. |
| 55 | H | 2-CH$_3$-5-Cl | H | C$_2$H$_5$ | 172.7° C. |
| 56 | H | 2-CH$_3$-5-Cl | H | n-C$_3$H$_7$ | 167.9° C. |
| 57 | H | 2-CH$_3$-5-Cl | H | i-C$_3$H$_7$ | 182.4° C. |
| 58 | H | 2-CH$_3$-5-Cl | H | n-C$_4$H$_9$ | 147.6° C. |
| 59 | H | 2-CH$_3$-5-Cl | H | i-C$_4$H$_9$ | |
| 60 | H | 2-CH$_3$-5-Cl | H | n-C$_5$H$_{11}$ | 143.8° C. |
| 61 | H | 2-CH$_3$-5-Cl | H | c-C$_4$H$_7$ | 128.1° C. |
| 62 | H | 2-CH$_3$-5-Cl | H | c-C$_5$H$_9$ | 133.7° C. |
| 63 | H | 2-CH$_3$-5-Cl | H | c-C$_6$H$_{11}$ | 175.0° C. |
| 64 | H | 2-CH$_3$-5-Cl | H | CH$_2$CH=CH$_2$ | 158.2° C. |
| 65 | H | 2-CH$_3$-5-Cl | H | CH$_2$CH$_2$N(CH$_3$)$_2$ | 103.5° C. |
| 66 | H | 2-CH$_3$-5-Cl | \multicolumn{2}{l}{—(CH$_2$)$_2$—N(CH$_2$—Ph)—(CH$_2$)$_2$—} | 160.4° C. |
| 67 | H | 2-CH$_3$-5-F | H | i-C$_4$H$_9$ | 159.5° C. |
| 68 | H | 2-CH$_3$-5-F | H | c-C$_4$H$_7$ | 151.3° C. |
| 69 | H | 2-CH$_3$-5-F | H | c-C$_5$H$_9$ | 154.7° C. |
| 70 | H | 2,6-(CH$_3$)$_2$ | H | n-C$_3$H$_7$ | 149.4° C. |
| 71 | H | 2,6-(CH$_3$)$_2$ | H | i-C$_3$H$_7$ | 155.6° C. |
| 72 | H | 2,6-(CH$_3$)$_2$ | H | i-C$_4$H$_9$ | 145.0° C. |
| 73 | H | 2,6-(C$_2$H$_5$)$_2$ | H | C$_2$H$_5$ | 160.5° C. |
| 74 | H | 2,6-(C$_2$H$_5$)$_2$ | H | i-C$_4$H$_9$ | 140.3° C. |
| 75 | H | 2,6-(C$_2$H$_5$)$_2$ | H | c-C$_5$H$_9$ | 178.5° C. |
| 76 | H | 2,6-(C$_2$H$_5$)$_2$ | H | c-C$_6$H$_{11}$ | 183.8° C. |
| 77 | H | 2,6-(C$_2$H$_5$)$_2$ | H | CH$_2$CH=CH$_2$ | 135.3° C. |
| 78 | H | 2,6-(C$_2$H$_5$)$_2$ | H | CH$_2$CH$_2$N(CH$_3$)$_2$ | 103.5° C. |
| 79 | H | 2-C$_2$H$_5$-6-CH$_3$ | H | n-C$_3$H$_7$ | 126.3° C. |
| 80 | H | 2-C$_2$H$_5$-6-CH$_3$ | H | i-C$_3$H$_7$ | 127.0° C. |
| 81 | H | 2-C$_2$H$_5$-6-CH$_3$ | H | i-C$_4$H$_9$ | 148.0° C. |
| 82 | H | 2-OCH$_3$-5-NO$_2$ | H | i-C$_4$H$_9$ | 159.3° C. |
| 83 | H | 2-OCH$_3$-5-NO$_2$ | H | c-C$_5$H$_9$ | 178.9° C. |
| 84 | H | 2-OCH$_3$-5-CH$_3$ | H | i-C$_4$H$_9$ | 168.2° C. |
| 85 | H | 2-OCH$_3$-5-CH$_3$ | H | c-C$_5$H$_9$ | 121.8° C. |
| 86 | H | 2,5-(OC$_2$H$_5$)$_2$ | H | i-C$_4$H$_9$ | 169.3° C. |
| 87 | H | 2,5-(OC$_2$H$_5$)$_2$ | H | c-C$_5$H$_9$ | 127.7° C. |
| 88 | 4-CH$_3$ | 2-CH$_3$-5-Cl | H | i-C$_4$H$_9$ | 166.6° C. |
| 89 | 4-CH$_3$ | 2-CH$_3$-5-Cl | H | c-C$_5$H$_9$ | 174.2° C. |
| 90 | 5-CH$_3$ | 2-CH$_3$-3-Cl | H | i-C$_4$H$_9$ | 160.5° C. |
| 91 | 5-CH$_3$ | 2-CH$_3$-3-Cl | H | n-C$_5$H$_{11}$ | 158–160° C. |
| 92 | 5-CH$_3$ | 2-CH$_3$-3-Cl | H | i-C$_5$H$_{11}$ | 135.5–136.0° C. |
| 93 | 5-CH$_3$ | 2-CH$_3$-3-Cl | H | CH$_2$CH(CH$_3$)C$_2$H$_5$ | 104–105° C. |
| 94 | 5-CH$_3$ | 2-CH$_3$-3-Cl | H | CH(CH$_3$)C$_3$H$_7$-n | 138–139° C. |

TABLE 1-continued (R3 is hydrogen atom and n is 0.)

$$\text{(I)}$$

Structure: Pyridine with $R_1$ at 5-position, $C(=O)-N(R_3)$-phenyl-$R_2$ at 3-position, $C(=O)-N(R_4)R_5$ at 2-position, N-$(O)_n$ at 1-position.

| No. | $R_1$ | $R_2$ | $R_4$ | $R_5$ | Melting point or refractive index |
|---|---|---|---|---|---|
| 95 | 5-$CH_3$ | 2-$CH_3$-3-Cl | H | $CH_2CH_2Cl$ | 152–153° C. |
| 96 | 5-$CH_3$ | 2-$CH_3$-3-Cl | H | $CH_2CH_2CH_2Cl$ | 143–147° C. |
| 97 | 5-$CH_3$ | 2-$CH_3$-3-Cl | H | $CH_2C(CH_3)=CH_2$ | 150–151° C. |
| 98 | 5-$CH_3$ | 2-$CH_3$-3-Cl | H | $CH_2$-c-$C_3H_5$ | 179° C. |
| 99 | 5-$CH_3$ | 2,6-$(C_2H_5)_2$ | H | i-$C_4H_9$ | 142.6° C. |
| 100 | 6-$CH_3$ | 2-$CH_3$-3-Cl | H | n-$C_3H_7$ | 144–146° C. |
| 101 | 6-$CH_3$ | 2-$CH_3$-3-Cl | H | i-$C_3H_7$ | 196.3° C. |
| 102 | 6-$CH_3$ | 2-$CH_3$-3-Cl | H | i-$C_4H_9$ | 157–159° C. |
| 103 | 6-$CH_3$ | 2-$CH_3$-3-Cl | H | s-$C_4H_9$ | 175° C. |
| 104 | 6-$CH_3$ | 2-$CH_3$-3-Cl | H | n-$C_4H_9$ | 165.7° C. |
| 105 | 6-$CH_3$ | 2-$CH_3$-3-Cl | H | n-$C_5H_{11}$ | 135° C. |
| 106 | 6-$CH_3$ | 2-$CH_3$-3-Cl | H | i-$C_5H_{11}$ | 146° C. |
| 107 | 6-$CH_3$ | 2-$CH_3$-3-Cl | H | $CH_2CH(CH_3)C_2H_5$ | 156–157° C. |
| 108 | 6-$CH_3$ | 2-$CH_3$-3-Cl | H | $CH_2C(CH_3)_3$ | 162° C. |
| 109 | 6-$CH_3$ | 2-$CH_3$-3-Cl | H | $CH(CH_3)C_3H_7$-n | 141° C. |
| 110 | 6-$CH_3$ | 2-$CH_3$-3-Cl | H | $CH_2C(CH_3)=CH_2$ | 177–178° C. |
| 111 | 6-$CH_3$ | 2-$CH_3$-3-Cl | H | c-$C_4H_7$ | 189.5–190.5° C. |
| 112 | 6-$CH_3$ | 2-$CH_3$-3-Cl | H | c-$C_5H_9$ | 161.9° C. |
| 113 | 6-$CH_3$ | 2-$CH_3$-3-Cl | H | $CH_2$-c-$C_3H_5$ | 177.5–178.0° C. |
| 114 | 6-$CH_3$ | 2-$CH_3$-3-Cl | H | $CH_2$-c-$C_4H_7$ | 142–144° C. |
| 115 | 6-$CH_3$ | 2-$CH_3$-3-Cl | H | $CH_2$-c-$C_5H_9$ | 144–146° C. |
| 116 | 6-$CH_3$ | 2-$CH_3$-3-Cl | H | $CH_2$-(2-$Cl_2$-c-$C_3H_3$) | 158–160° C. |
| 117 | 6-$CH_3$ | 2-$CH_3$-3-Cl | H | $CH_2$-(2-$F_2$-c-$C_3H_3$) | 165–167° C. |
| 118 | 6-$CH_3$ | 2-$CH_3$-3-Cl | H | $CH_2CH_2Cl$ | 172–174° C. |
| 119 | 6-$CH_3$ | 2-$CH_3$-3-Cl | H | $CH_2CH_2CH_2Cl$ | 146–148° C. |
| 120 | 6-$CH_3$ | 2-$CH_3$-3-Cl | H | $CH_2CH_2CH_2F$ | 154–156° C. |
| 121 | 6-$CH_3$ | 2-$CH_3$-3-Cl | H | $CH_2CH_2SCH_3$ | 149–151° C. |
| 122 | 6-$CH_3$ | 2-$CH_3$-3-Cl | H | $CH_2$-Fury | 152.5–153.5° C. |
| 123 | 6-$CH_3$ | 2-$CH_3$-3-Br | H | n-$C_3H_7$ | 157–160° C. |
| 124 | 6-$CH_3$ | 2-$CH_3$-3-Br | H | i-$C_4H_9$ | 164–166° C. |
| 125 | 6-$CH_3$ | 2-$CH_3$-3-Br | H | $CH_2C(CH_3)_3$ | 165–166° C. |
| 126 | 6-$CH_3$ | 2-$CH_3$-3-Br | H | c-$C_5H_9$ | 199–201° C. |
| 127 | 6-$CH_3$ | 2-$CH_3$-3-F | H | n-$C_3H_7$ | 126–131° C. |
| 128 | 6-$CH_3$ | 2-$CH_3$-3-F | H | i-$C_4H_9$ | 151–153° C. |
| 129 | 6-$CH_3$ | 2-$CH_3$-3-F | H | c-$C_5H_9$ | 163–165° C. |
| 130 | 6-$CH_3$ | 2-$CH_3$-3-I | H | n-$C_3H_7$ | 170–173° C. |
| 131 | 6-$CH_3$ | 2-$CH_3$-3-I | H | i-$C_4H_9$ | 175–176° C. |
| 132 | 6-$CH_3$ | 2-$CH_3$-3-I | H | c-$C_5H_9$ | 196–198° C. |
| 133 | 6-$CH_3$ | 2-$CH_3$-3-CN | H | n-$C_3H_7$ | 184–186° C. |
| 134 | 6-$CH_3$ | 2-$CH_3$-3-CN | H | c-$C_5H_9$ | 171–172° C. |
| 135 | 6-$CH_3$ | 2-$CH_3$-3-$OCHF_2$ | H | n-$C_3H_7$ | 149–151° C. |
| 136 | 6-$CH_3$ | 2-$CH_3$-3-$OCHF_2$ | H | i-$C_4H_9$ | 133–135° C. |
| 137 | 6-$CH_3$ | 2-$CH_3$-3-$OCHF_2$ | H | c-$C_5H_9$ | 166–168° C. |
| 138 | 6-$CH_3$ | 2-$CH_3$-5-Cl | H | $C_2H_5$ | 180.2° C. |
| 139 | 6-$CH_3$ | 2-$CH_3$-5-Cl | H | n-$C_3H_7$ | 163.3° C. |
| 140 | 6-$CH_3$ | 2-$CH_3$-5-Cl | H | i-$C_3H_7$ | 168.1° C. |
| 141 | 6-$CH_3$ | 2-$CH_3$-5-Cl | H | i-$C_4H_9$ | 124.6° C. |
| 142 | 6-$CH_3$ | 2-$CH_3$-5-Cl | H | $CH_2CH=CH_2$ | 177.6° C. |
| 143 | 6-$CH_3$ | 2-$CH_3$-5-Cl | H | $CH_2C\equiv CH$ | 196.0° C. |
| 144 | 6-$CH_3$ | 2-$CH_3$-5-F | H | i-$C_4H_9$ | 142.5° C. |
| 145 | 6-$CH_3$ | 2-$CH_3$-5-F | H | c-$C_5H_9$ | 182.3° C. |
| 146 | 6-$CH_3$ | 2-$C_2H_5$-5-Cl | H | i-$C_4H_9$ | 154.4° C. |
| 147 | 6-$CH_3$ | 2-$C_2H_5$-5-Cl | H | c-$C_5H_9$ | 173.1° C. |
| 148 | 6-$CH_3$ | 2,5-$(CH_3)_2$ | H | i-$C_4H_9$ | 125.9° C. |
| 149 | 6-$CH_3$ | 2,5-$(CH_3)_2$ | H | c-$C_5H_9$ | 181.7° C. |
| 150 | 6-$CH_3$ | 2,6-$(C_2H_5)_2$ | H | $CH_2CH=CH_2$ | 160.1° C. |
| 151 | 5-$C_2H_5$ | 2-$CH_3$-3-Cl | H | n-$C_3H_7$ | 127–128° C. |
| 152 | 5-$C_2H_5$ | 2-$CH_3$-3-Cl | H | i-$C_3H_7$ | 165–166° C. |
| 153 | 5-$C_2H_5$ | 2-$CH_3$-3-Cl | H | n-$C_4H_9$ | 135° C. |

TABLE 1-continued (R3 is hydrogen atom and n is 0.)

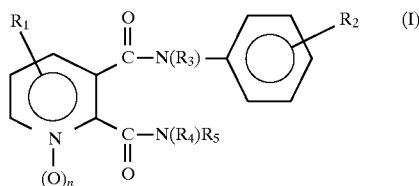

| No. | $R_1$ | $R_2$ | $R_4$ | $R_5$ | Melting point or refractive index |
|---|---|---|---|---|---|
| 154 | 5-$C_2H_5$ | 2-$CH_3$-3-Cl | H | i-$C_4H_9$ | 147° C. |
| 155 | 5-$C_2H_5$ | 2-$CH_3$-3-Cl | H | s-$C_4H_9$ | 152° C. |
| 156 | 5-$C_2H_5$ | 2-$CH_3$-3-Cl | H | i-$C_5H_{11}$ | 116.5–117.0° C. |
| 157 | 5-$C_2H_5$ | 2-$CH_3$-3-Cl | H | $CH_2CH(CH_3)C_2H_5$ | 116–117° C. |
| 158 | 5-$C_2H_5$ | 2-$CH_3$-3-Cl | H | $CH(CH_3)C_3H_7$-n | 119–120° C. |
| 159 | 5-$C_2H_5$ | 2-$CH_3$-3-Cl | H | $CH_2C(CH_3)_3$ | 147–148° C. |
| 160 | 5-$C_2H_5$ | 2-$CH_3$-3-Cl | H | $CH_2C(CH_3)=CH_2$ | 123–124° C. |
| 161 | 5-$C_2H_5$ | 2-$CH_3$-3-Cl | H | c-$C_5H_9$ | 166–167° C. |
| 162 | 5-$C_2H_5$ | 2-$CH_3$-3-Cl | H | $CH_2$-c-$C_3H_5$ | 159.9° C. |
| 163 | 5-$C_2H_5$ | 2-$CH_3$-3-Cl | H | i-$C_4H_9$ | 163.5° C. |
| 164 | 5-$C_2H_5$ | 2,6-$(C_2H_5)_2$ | H | i-$C_4H_9$ | 102.3° C. |
| 165 | 6-$C_2H_5$ | 2-$CH_3$-3-Cl | H | n-$C_3H_7$ | 143–144° C. |
| 166 | 6-$C_2H_5$ | 2-$CH_3$-3-Cl | H | i-$C_4H_9$ | 147–148° C. |
| 167 | 6-$C_2H_5$ | 2-$CH_3$-3-Cl | H | c-$C_5H_9$ | 158–160° C. |
| 168 | 6-Cl | 2-$CH_3$-3-Cl | H | n-$C_3H_7$ | 173.5–174.5° C. |
| 169 | 6-Cl | 2-$CH_3$-3-Cl | H | $CH_2$-c-$C_5H_9$ | 188° C. |
| 170 | 6-Cl | 2-$CH_3$-3-Cl | H | i-$C_4H_9$ | 158–160° C. |
| 171 | 6-Cl | 2-$CH_3$-3-Cl | H | c-$C_5H_9$ | 187–188° C. |
| 172 | 6-Cl | 2-$CH_3$-3-Cl | H | $CH_2C(CH_3)_3$ | 187.5–188.5° C. |
| 173 | 6-Br | 2-$CH_3$-3-Cl | H | n-$C_3H_7$ | 187–188° C. |
| 174 | 6-Br | 2-$CH_3$-3-Cl | H | i-$C_4H_9$ | 181–183° C. |
| 175 | 6-Br | 2-$CH_3$-3-Cl | H | c-$C_5H_9$ | 204–206° C. |
| 176 | 6-$SCH_3$ | 2-$CH_3$-3-Cl | H | n-$C_3H_7$ | 164° C. |
| 177 | 6-$SCH_3$ | 2-$CH_3$-3-Cl | H | i-$C_4H_9$ | 181–182° C. |
| 178 | 6-$SCH_3$ | 2-$CH_3$-3-Cl | H | c-$C_5H_9$ | 184–185° C. |
| 179 | 6-$SCH_3$ | 2-$CH_3$-3-Cl | H | $CH_2C(CH_3)_3$ | 181° C. |
| 180 | 6-$SC_3H_7$-n | 2-$CH_3$-3-Cl | H | n-$C_3H_7$ | 156–157° C. |
| 181 | 6-$SC_3H_7$-n | 2-$CH_3$-3-Cl | H | i-$C_4H_9$ | 173–175° C. |
| 182 | 6-$SC_3H_7$-n | 2-$CH_3$-3-Cl | H | c-$C_5H_9$ | 176–179° C. |
| 183 | 6-$SC_4H_9$-i | 2-$CH_3$-3-Cl | H | n-$C_3H_7$ | 170–172° C. |
| 184 | 6-$SC_4H_9$-i | 2-$CH_3$-3-Cl | H | c-$C_5H_9$ | 195–197° C. |
| 185 | 6-S-Ph | 2-$CH_3$-3-Cl | H | n-$C_3H_7$ | 152.5–153.0° C. |
| 186 | 6-S-Ph | 2-$CH_3$-3-Cl | H | i-$C_4H_9$ | 148.5–149.5° C. |
| 187 | 6-S-Ph | 2-$CH_3$-3-Cl | H | c-$C_5H_9$ | 177–178° C. |
| 188 | 5-(CH=CH—CH=CH)-6 | 2-$CH_3$-3-Cl | H | n-$C_3H_7$ | 198–200° C. |
| 189 | 5-(CH=CH—CH=CH)-6 | 2-$CH_3$-3-Cl | H | i-$C_3H_7$ | 224–226° C. |
| 190 | 5-(CH=CH—CH=CH)-6 | 2-$CH_3$-3-Cl | H | i-$C_4H_9$ | 193–195° C. |
| 191 | 5-(CH=CH—CH=CH)-6 | 2-$CH_3$-3-Cl | H | c-$C_5H_9$ | 199–201° C. |
| 192 | 5-$(CH_2)_4$-6 | 2-$CH_3$-5-Cl | H | i-$C_3H_7$ | 154.0° C. |
| 193 | 5-$(CH_2)_4$-6 | 2-$CH_3$-5-Cl | H | c-$C_5H_9$ | 197.3° C. |
| 194 | 5-$(CH_2)_3$-6 | 2-$CH_3$-5-Cl | H | i-$C_4H_9$ | 142.3° C. |
| 195 | 5-$(CH_2)_3$-6 | 2-$CH_3$-5-Cl | H | c-$C_5H_9$ | 168.5° C. |
| 196 | 6-$CH_3$ | 2,3-$Cl_2$ | H | c-$C_5H_9$ | 196–197° C. |
| 197 | 6-$CH_3$ | 2,3-$Cl_2$ | H | n-$C_3H_7$ | 170.5–171.5° C. |
| 198 | 6-$CH_3$ | 2,3-$Cl_2$ | H | i-$C_4H_9$ | 164–166° C. |
| 199 | 6-$CH_3$ | 2,6-$(C_2H_5)_2$-3-Cl | H | c-$C_5H_9$ | 136–138° C. |
| 200 | 6-$CH_3$ | 2,6-$(C_2H_5)_2$-3-Cl | H | n-$C_3H_7$ | 169–171° C. |
| 201 | 6-$CH_3$ | 2,6-$(C_2H_5)_2$-3-Cl | H | i-$C_4H_9$ | 175.0–175.5° C. |

TABLE 1-continued (R3 is hydrogen atom and n is 0.)

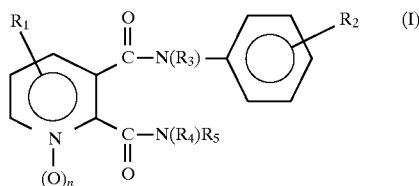

| No. | $R_1$ | $R_2$ | $R_4$ | $R_5$ | Melting point or refractive index |
|---|---|---|---|---|---|
| 202 | 6-$C_2H_5$S | 2-$CH_3$-3-Cl | H | c-$C_5H_9$ | 179–181° C. |
| 203 | 6-$C_2H_5$S | 2-$CH_3$-3-Cl | H | n-$C_3H_7$ | 168–169° C. |
| 204 | 6-$CH_3$ | 4-$CF_3$ | H | c-$C_5H_9$ | 185–187° C. |
| 205 | 6-$CH_3$ | 4-$CF_3$ | H | n-$C_3H_7$ | 192–193° C. |
| 206 | 6-c-$C_3H_5$ | 2-$CH_3$-3-Cl | H | c-$C_5H_9$ | 201–202° C. |
| 207 | 4,6-(c-$C_3H_5$)$_2$ | 2-$CH_3$-3-Cl | H | c-$C_5H_9$ | 219–220° C. |
| 208 | 6-(2,4-$Cl_2$—$C_6H_3$—O) | 2-$CH_3$-3-Cl | H | n-$C_3H_7$ | 162–164° C. |
| 209 | 6-(2,4-$Cl_2$—$C_6H_3$—O) | 2-$CH_3$-3-Cl | H | c-$C_5H_9$ | 184–185° C. |
| 210 | 6-$CH_3$ | 2,6-($C_2H_5$)$_2$-3-Cl | H | neo-$C_5H_{11}$ | 55-60° C. |
| 211 | 5-(CH=CH—CH=CH)-6 | 2-$CH_3$-3-Cl | H | neo-$C_5H_{11}$ | 203–206° C. |
| 212 | 5-(CH=CH—CH=CH)-6 | 2-$CH_3$-3-Cl | H | $C_2H_5$ | 221–222° C. |
| 213 | 6-$CH_3$ | 2-$CH_3$-3-COO$CH_3$ | H | n-$C_3H_7$ | 137–139° C. |
| 214 | 6-$CH_3$ | 2-$CH_3$-3-COO$CH_3$ | H | c-$C_5H_9$ | 161–163° C. |
| 215 | 6-$CH_3$ | 2-$CH_3$-3-$CF_3$ | H | c-$C_5H_9$ | 169–170° C. |
| 216 | 6-$CH_3$ | 2-$CH_3$-3-$CF_3$ | H | n-$C_3H_7$ | 163–165° C. |
| 217 | 6-$CH_3$ | 2-$CH_3$-3-$CF_3$ | H | neo-$C_5H_{11}$ | 169–171° C. |
| 218 | 6-$CH_3$ | 2,6-($C_2H_5$)$_2$-3-Cl | H | $C_2H_5$ | 169–171° C. |
| 219 | 6-$CH_3$ | 2,6-($C_2H_5$)$_2$-3,5-$Cl_2$ | H | n-$C_3H_7$ | 191–193° C. |
| 220 | 6-$CH_3$ | 2,6-($C_2H_5$)$_2$-3,5-$Cl_2$ | H | neo-$C_5H_{11}$ | 177–178° C. |
| 221 | 6-$CH_3$ | 2,6-($C_2H_5$)$_2$-3,5-$Cl_2$ | H | c-$C_5H_9$ | 186–188° C. |
| 222 | 6-$CH_3$ | 3,4-$Cl_2$ | H | n-$C_3H_7$ | 198–200° C. |
| 223 | 6-$CH_3$ | 3,4-$Cl_2$ | H | c-$C_5H_9$ | 186–188° C. |
| 224 | 6-$CH_3$ | 2,6-($C_2H_5$)$_2$-3,5-$Cl_2$ | H | $C_2H_5$ | 219–221° C. |
| 225 | 6-$CH_3$ | 2,6-($C_2H_5$)$_2$-3,5-$Cl_2$ | H | i-$C_4H_9$ | 185–186° C. |
| 226 | 6-$CH_3$ | 2-$CH_3$-3-O$CH_2$COO$CH_3$ | H | n-$C_3H_7$ | 118–122° C. |
| 227 | 6-$CH_3$ | 2-$CH_3$-3-O$CH_2$COO$CH_3$ | H | c-$C_5H_9$ | 148–154° C. |
| 228 | 6-Cl | 2,6-($C_2H_5$)$_2$-3,5-$Cl_2$ | H | n-$C_3H_7$ | 165–167° C. |
| 229 | 6-Cl | 2,6-($C_2H_5$)$_2$-3,5-$Cl_2$ | H | i-$C_4H_9$ | 124–126° C. |
| 230 | 6-Cl | 2,6-($C_2H_5$)$_2$-3-Cl | H | neo-$C_5H_{11}$ | 150–152° C. |
| 231 | 6-Cl | 2,6-($C_2H_5$)$_2$-3-Cl | H | c-$C_5H_9$ | 149–151° C. |
| 232 | 6-$CH_3$S | 2,6-($C_2H_5$)$_2$-3-Cl | H | n-$C_3H_7$ | 153–155° C. |
| 233 | 6-$CH_3$S | 2,6-($C_2H_5$)$_2$-3-Cl | H | i-$C_4H_9$ | 183–185° C. |
| 234 | 6-$CH_3$S | 2,6-($C_2H_5$)$_2$-3-Cl | H | neo-$C_5H_{11}$ | 188–190° C. |
| 235 | 6-$CH_3$S | 2,6-($C_2H_5$)$_2$-3-Cl | H | c-$C_5H_9$ | 68-70° C. |
| 236 | 6-$CH_3SO_2$ | 2,6-($C_2H_5$)$_2$-3-Cl | H | c-$C_5H_9$ | 221–223° C. |
| 237 | 6-$CH_3SO_2$ | 2,6-($C_2H_5$)$_2$-3-Cl | H | neo-$C_5H_{11}$ | 237–239° C. |
| 238 | 6-$CH_3SO_2$ | 2,6-($C_2H_5$)$_2$-3-Cl | H | c-$C_5H_9$ | 220–222° C. |
| 239 | 6-$CF_3$ | 2-$CH_3$-3-Cl | H | n-$C_3H_7$ | 190–191° C. |
| 240 | 6-$CF_3$ | 2-$CH_3$-3-Cl | H | i-$C_4H_9$ | 191–192° C. |
| 241 | 6-$CF_3$ | 2-$CH_3$-3-Cl | H | neo-$C_5H_{11}$ | 200–202° C. |
| 242 | 6-$CF_3$ | 2-$CH_3$-3-Cl | H | c-$C_5H_9$ | 216–218° C. |
| 243 | 6-$CF_3$ | 2,6-($C_2H_5$)$_2$-3-Cl | H | n-$C_3H_7$ | 180–182° C. |
| 244 | 6-$CF_3$ | 2,6-($C_2H_5$)$_2$-3-Cl | H | i-$C_4H_9$ | 166–168° C. |
| 245 | 6-$CF_3$ | 2,6-($C_2H_5$)$_2$-3-Cl | H | neo-$C_5H_{11}$ | 188–190° C. |
| 246 | 6-$CF_3$ | 2,6-($C_2H_5$)$_2$-3-Cl | H | c-$C_5H_9$ | 137–141° C. |
| 247 | 5-($CH_2$)$_4$-6 | 2,6-($C_2H_5$)$_2$-3-Cl | H | n-$C_3H_7$ | 211–213° C. |
| 248 | 5-($CH_2$)$_4$-6 | 2,6-($C_2H_5$)$_2$-3-Cl | H | c-$C_5H_9$ | 161–163° C. |
| 249 | 6-$CH_3$ | 2-$CH_3$-3-$NO_2$ | H | n-$C_3H_7$ | 171–173° C. |
| 250 | 6-$CH_3$ | 2-$CH_3$-3-$NO_2$ | H | c-$C_5H_9$ | 167–169° C. |

In Table 1, "c-" means an alicyclic hydrocarbon group, "Fury" means a tetrahydrofuran-2-yl group, and "Ph" means a phenyl group.

The herbicides comprising, as an active ingredient, the pyridine-2,3-dicarboxylic acid diamide derivative represented by the formula (I) are useful for controlling annual and perennial weeds which grow in paddy fields, upland fields, orchards, swamps, etc., such as barnyard grass (*Echinochloa crus-galli Beauv.*, an annual gramineous grass which is an injurious weed of paddy field), umbrella plant (*Cyperus difformis L.*, an annual cyperaceous grass which is an injurious weed of paddy fields), slender spikerush (*Eleocharis acicularis Roem.* et Schult, a perennial cyperaceous grass which is an injurious weed of paddy fields and which grows also in swamps and waterways), arrowhead (*Saquittaria pygmaea Mig.*, an injurious perennial weed of Alismataceae family which grows in paddy fields, swamps and ditches), bulrush (*Scirpus juncoides Roxb.* var. hotarui ohwi, a perennial cyperaceous weed which grows in paddy fields, swamps and ditches), foxtail grass (*Alopecurus aegualis* var. *amurensis Ohwi*, gramineous grass which grows in paddy fields and low swamps), wild oats (*Avena fatua L.*, a biennial graminous grass which grows in plains, waste lands and upland fields), mugwort (*Artemisia princess Pamp.*, a perennial composite grass which grows in cultivated and uncultivated fields and mountains), large crabgrass (*Digitaria adscendcus Henr.*, an annual gramineous grass which is a strongly injurious weed of upland fields and orchards), Gishigishi or Japanese dock (*Rumex japonicus Houtt.*, a perennial polygonaceous weed which grows in upland fields and roadsides), umbrella sedge (*Cyperus iria L.*, an annual cyperaceous weed), redroot pigweed (*Amaranthus varidis L.*, an annual weed of Amaranthaceae family which grows in vacant lands, roadsides and upland fields), cocklebur (*Xanthium strumarium L.*, an injurious annual composite weed which grows in upland fields), velvetleaf (*Abutilon theophrasti L.*, an injurious annual weed of Malvaceae family which grows in upland fields), purple thornapple (*Dutura tatula L.*, an annual injurious weed of Convolvulaceae family which grows in upland fields), bird's eye speedwell (*Veronica persica Poir.*, an injurious biennual weed of Scrophulariaceae family which grows in upland fields) and cleavers (*Galium aparine L.*, an injurious annual weed of Rubiaceae family which grows in upland fields and orchards), and especially useful for controlling weeds such as barnyard grass and bulrush in paddy fields.

Since the herbicides comprising, as an active ingredient, the pyridine-2,3-dicarboxylic acid diamide derivative represented by the formula (I) exhibit an excellent controlling effect on weeds before or after emergence, the characteristic physiological activities of the herbicides can be effectively manifested by treating fields with the herbicides before planting useful plants therein, or after planting useful plants therein (including the case in which useful plants are already planted as in orchards) but during the period from the initial stage of emergence of weeds to their growth stage.

However, the application of the herbicides of the present invention is not restricted only to the modes mentioned above. The herbicides of the present invention can be applied to control not only weeds which grow in paddy fields but also weeds which grow in other places such as uplands, temporarily non-cultivated paddy fields and upland fields, ridges between fields, agricultural pathways, waterways, lands constructed for pasture, graveyards, roads, playgrounds, unoccupied areas around buildings, developed lands, railways, forests and the like.

The treatment of target fields with the herbicides is most effective in economy when the treatment is made by the initial stage of emergence of weeds. However, the treatment is not restricted thereto and can be carried out even during the growth stage of weeds.

For applying the pyridine-2,3-dicarboxylic acid diamide derivatives represented by the formula (I) as herbicides, they are generally formulated into a form convenient to use according to the procedure conventionally employed for preparing agricultural chemicals.

That is, the pyridine-2,3-dicarboxylic acid diamide derivative represented by the formula (I) is mixed with a suitable inert carrier and, as necessary, further with an adjuvant, in an appropriate ratio, and the mixture is made into a desired form of preparation, such as suspension, emulsifiable concentrate, solution, wettable powder, granules, dust, tablets and the like, through dissolution, dispersion, suspension, mixing, impregnation, adsorption or adhesion.

The inert carriers usable in the present invention may be solid or liquid. Materials usable as the solid carriers include, for example, soybean flour, cereal flour, wood flour, bark flour, saw dust, powdered tobacco stalks, powdered walnut shells, bran, powdered cellulose, extraction residues of vegetables, powdered synthetic polymers or resins, clays (e.g. kaolin, bentonite and acid clay), talcs (e.g. talc and pyrophyllite), silica powders or flakes [e.g. diatomaceous earth, silica sand, mica and white carbon (i.e. highly dispersed silicic acid, also called finely divided hydrated silica or hydrated silicic acid)], activated carbon, powdered sulfur, powdered pumice, calcined diatomaceous earth, ground brick, fly ash, sand, calcium carbonate powder, calcium phosphate powder, other inorganic mineral powders, chemical fertilizers (e.g. ammonium sulfate, ammonium phosphate, ammonium nitrate, urea, and ammonium chloride) and compost. These materials can be used alone or in combination of two or more.

Materials usable as the liquid carriers are selected not only from those which have solvency by themselves but also from those which have no solvency but capable of dispersing the active ingredient compound with the aid of adjuvants. Typical examples of the liquid carriers, which can be used alone or in combination of two or more, are water, alcohols (e.g. methanol, ethanol, isopropanol, butanol and ethylene glycol), ketones (e.g. acetone, methyl ethyl ketone, methyl isobutyl ketone, diisobutyl ketone and cyclohexanone), ethers (e.g. ethyl ether, dioxane, Cellosolve, dipropyl ether and tetrahydrofuran), aliphatic hydrocarbons (e.g. kerosene and mineral oils), aromatic hydrocarbons (e.g. benzene, toluene, xylene, solvent naphtha and alkyl-naphthalenes), halogenated hydrocarbons (e.g. dichloro-ethane, chloroform and carbon tetrachloride), esters (e.g. ethyl acetate, diisopropyl phthalate, dibutyl phthalate and dioctyl phthalate), amides (e.g. dimethylformamide, diethylformamide and dimethylacetamide), nitriles (e.g. acetonitrile), and dimethyl sulfoxide.

As the adjuvants, there can be mentioned the following typical adjuvants. They are used according to respective purpose. They may be used alone or in combination of two or more, or may not be used at all.

For the purpose of emulsifying, dispersing, solubilizing and/or wetting the active ingredient compounds, there are used surface active agents, for example, polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalenesulfonic acid condensation products, ligninsulfonates and higher alcohol sulfate esters.

For the purpose of imparting stable dispersion, tackiness and/or bonding property to the active ingredient compounds, there may be used adjuvants such as casein, gelatin, starch, methyl cellulose, carboxy-methyl cellulose, gum arabic, polyvinyl alcohol, turpentine, bran oil, bentonite and ligninsulfonates.

For the purpose of improving the flow properties of solid herbicidal compositions, there may be used adjuvants such as waxes, stearates and alkyl phosphates.

Adjuvants such as naphthalenesulfonic acid condensation products and polyphosphates may be used as peptizers in dispersible herbicidal compositions.

Adjuvants such as silicone oils may be used as defoaming agent.

The content of the active ingredient compound may be varied as occasion demands. For example, for the preparation of a powdered or granulated product, the content is suitably 0.01–50% by weight, and for the preparation of an emulsifiable concentrate or a wettable powder, the content is also suitably 0.01–50% by weight as well.

For controlling various weeds or inhibiting their growth, the herbicides comprising, as an active ingredient, the pyridine-2,3-dicarboxylic acid diamide derivative represented by the formula (I) are applied as such or after appropriately diluted with or suspended in water or other media, in an amount effective for controlling weeds or inhibiting their growth, to the foliage and stalks of the weeds or to soil in the area where the emergence or growth of the weeds is undesirable.

The amount of herbicides comprising, as an active ingredient, the pyridine-2,3-dicarboxylic acid diamide derivative represented by the formula (I) used varies depending on various factors, for example, the purpose of application, the kinds of target weeds, the growth states of crops, the emergence tendency of weeds, weather, environmental conditions, the form of the herbicides used, the mode of application, the type or state of application site and the time of application. However, the amount is selected appropriately according to the purpose from the range of 0.1 g to 10 kg in terms of the amount of active ingredient compound per hectare.

The herbicides containing, as an active ingredient, the pyridine-2,3-dicarboxylic acid diamide derivative represented by the formula (I) can be applied jointly with other herbicides for the purpose of expanding both the spectrum of controllable weeds and the period of time when effective application is possible or for the purpose of reducing the dosage.

EXAMPLES OF THE INVENTION

The compounds represented by the formula (IV-1) or (IV-2) which are starting materials for producing the pyridine-2,3-dicarboxylic acid diamide derivatives represented by the formula (I) can be easily produced by the procedure described in J. Indian Chem. Soc. 11, 707–10 or from quinolinic acid anhydride derivatives and substituted anilines.

Example 1
1-1. Production of 2-(2-methyl-3-chlorophenyl)amino-carbonyl-3-pyridinecarboxylic acid

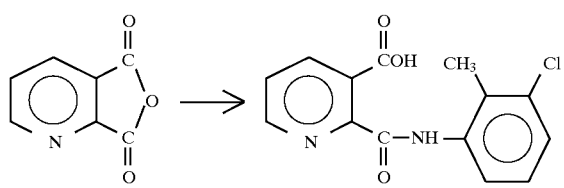

7.08 g (47.5 mM) of 2,3-pyridinecarboxylic acid anhydride was dissolved in 120 ml of anhydrous tetrahydrofuran. To the solution under stirring was added a solution of 2-amino-6-chlorotoluene (6.72 g, 47.5 mM) in anhydrous tetrahydrofuran (20 ml), and a reaction was carried out at room temperature for 12 hours.

After completion of the reaction, the reaction mixture was subjected to vacuum distillation and the precipitated crystal was washed with a small amount of ether to obtain 12.72 g of the intended product having a melting point of 148°–151° C., at a yield of 92%.

1-2. Production of N-(2-methyl-3-chlorophenyl)-2,3-pyridinedicarboxyimide

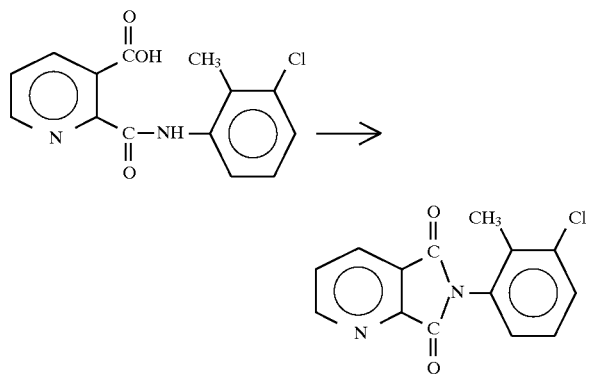

10.0 g (34.4 mM) of 2-(2-methyl-3-chloro-phenyl)aminocarbonyl-3-pyridinecarboxylic acid was dissolved in 30 ml of trifluoroacetic acid. To the solution was added 7.22 g (34.4 mM) of trifluoroacetic anhydride, and a reaction was carried out for 3 hours under reflux.

After completion of the reaction, the reaction mixture was subjected to vacuum distillation, and the resulting solid was dissolved in ethyl acetate. The solution was washed with saturated sodium hydrogen-carbonate and saturated aqueous sodium chloride solution in succession, and dried over anhydrous magnesium sulfate. The solvent was distilled off under reduced pressure and the resulting solid was washed with a small amount of ether to obtain 7.32 g of the intended product having a melting point of 204° C., at a yield of 78%.

1-3. Production of 3-(2-methyl-3-chlorophenyl)amino-carbonyl-2-pyridinecarboxylic acid n-propylamide (compound No. 11)

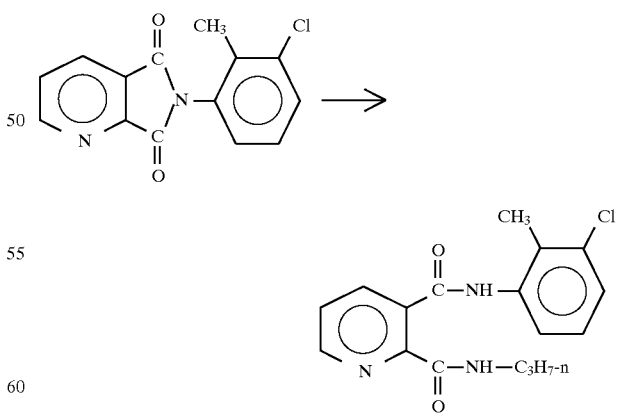

0.70 g (2.6 mM) of N-(2-methyl-3-chlorophenyl)-2,3-pyridinedicarboxyimide was dissolved in 15 ml of dioxane. To the solution was added 0.31 g (5.1 mM) of n-propylamine, and a reaction was carried out at room temperature for 12 hours.

After completion of the reaction, the reaction mixture was subjected to vacuum distillation, and the resulting residue was purified by silica gel column chromatography using ethyl acetate/n-hexane/chloroform as an eluent to obtain 0.79 g of the intended product as a white crystal having a melting point of 153.5°–154.5° C., at a yield of 92%.

Example 2

Production of 3-(2-methyl-3-chlorophenyl)-aminocarbonyl-2-pyridinecarboxylic acid methylamide (compound No. 9)

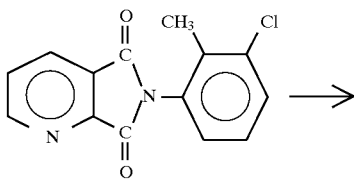

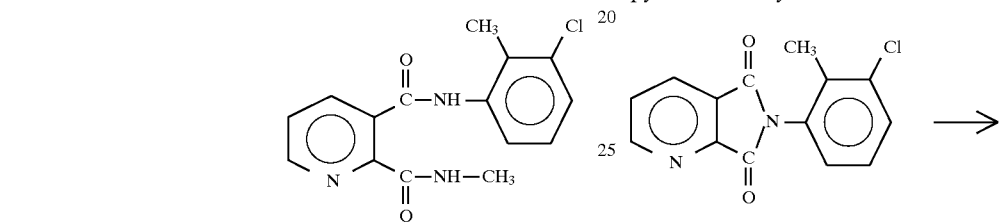

0.55 g (2.0 mM) of N-(2-methyl-3-chloro- phenyl)-2,3-pyridinedicarboxyimide was dissolved in 13 ml of dioxane. To the solution were added 0.27 g (4.0 mM) of methylamine hydrochloride and 0.51 g (5.1 mM) of triethylamine, and a reaction was carried out at room temperature for 36 hours.

After completion of the reaction, ethyl acetate was added to the reaction mixture and the solution was washed with saturated sodium hydrogen-carbonate and saturated aqueous sodium chloride solution in succession, and dried over anhydrous magnesium sulfate. The solvent was distilled off under reduced pressure, and the resulting residue was purified by silica gel column chromatography using ethyl acetate/n-hexane/chloroform as an eluent to obtain 0.47 g of the intended product as a white crystal having a melting point of 175°–176° C. at a yield of 80%.

Example 3

3-1. Production of N-(2-methyl-3-chlorophenyl)-2,3-pyridinecarboxyimide

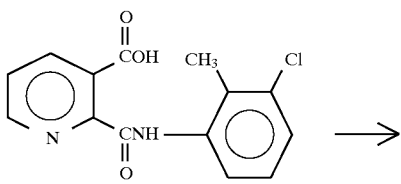

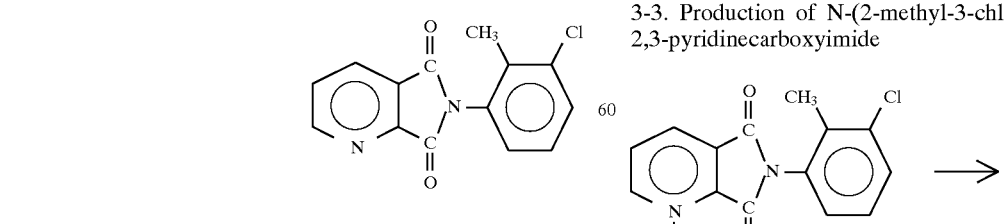

10.0 g (34.4 mM) of 2-(2-methyl-3-chloro-phenyl) aminocarbonyl-3-pyridinedicarboxylic acid was dissolved in tetrahydrofuran (100 ml). To the solution under cooling with ice was slowly added dropwise a tetrahydrofuran suspension containing 1.33 g (34.4 mM) of sodium hydride (62%). It was confirmed by a bubbler that no gas was generated. Then, a solution of 4.58 g (36.1 ml) of oxalyl chloride in tetrahydrofuran was added dropwise. It was again confirmed by a bubbler that no gas was generated, followed by carrying out the reaction for 1 hour under reflux. After completion of the reaction, the reaction mixture was extracted with ethyl acetate and the solution was washed with saturated aqueous sodium carbonate solution and saturated aqueous sodium chloride solution in succession, and dried over anhydrous magnesium sulfate. The solvent was distilled off under reduced pressure and the resulting solid was washed with a small amount of ether to obtain 7.88 g (28.9 mM) of the intended product having a melting point of 204° C., at a yield of 84%.

3-2. Production of N-(2-methyl-3-chlorophenyl)-2,3-10 pyridinecarboxyimide-1-oxide

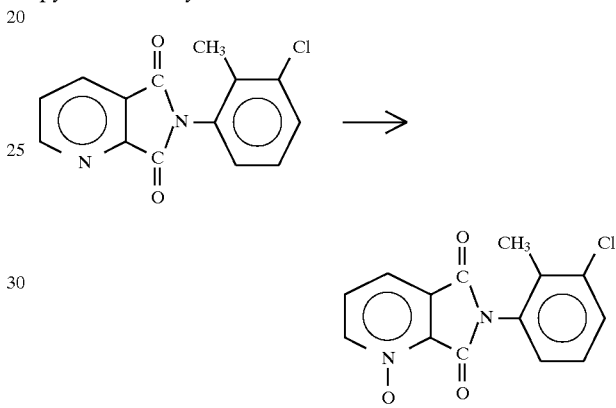

23.9 g (87.6 mM) of N-(2-methyl-3-chlorophenyl)-6-phenylthio-2,3-pyridinedicarboxyimide was dissolved in 300 ml of chloroform, and, then, to the solution was added 65.0 g (263 mM) of 70% 3-perchloro-benzoic acid, followed by carrying out the reaction for 24 hours under reflux.

After completion of the reaction, the reaction mixture was cooled to room temperature and ethyl acetate was added thereto. The organic layer was washed with saturated aqueous sodium carbonate solution thrice and then with saturated aqueous sodium chloride solution, and dried over magnesium sulfate, followed by concentration under reduced pressure. Diethyl ether was added to the resulting residue, followed by careful stirring to precipitate a crystal, which was filtered to obtain 10.9 g (37.9 mM) of the intended product (rough yield 43%).

$^1$H-NMR[TMS/CDCl$_3$, δ (ppm)]2.22(3H,s), 7.11(1H,dd, J=0.9 and 7.8 Hz), 7.28(1H,t,J=7.8 Hz), 7.51(1H,dd,J=0.9 and 7.8 Hz), 7.64(1H,brt,J=ca.6.9 Hz), 7.75(1H,d,J=7.2 Hz), 8.45(1H,d,J=6.3 Hz)

3-3. Production of N-(2-methyl-3-chlorophenyl)-6-chloro-2,3-pyridinecarboxyimide

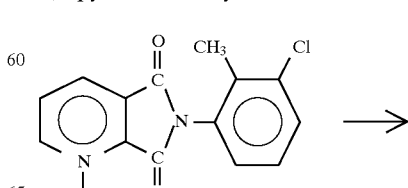

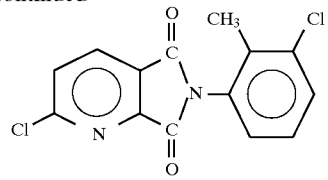
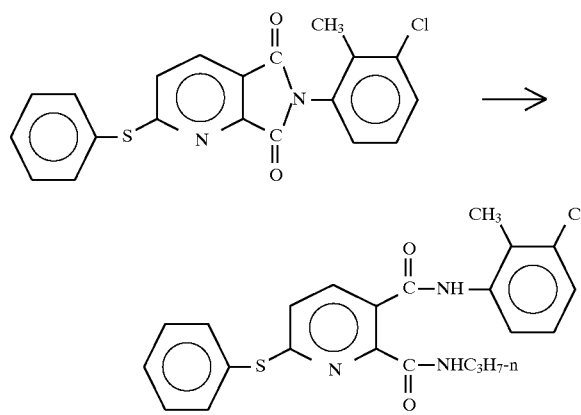

2.60 g (9.01 mM) of N-(2-methyl-3-chlorophenyl)-2,3-pyridinedicarboxyimide-1-oxide was dissolved in phosphorus oxychloride (25 ml) and, then, the solution was gradually heated and the reaction was carried out for 3 hours under reflux.

After completion of the reaction, the reaction mixture was cooled to room temperature and, then, excess phosphorus oxychloride was distilled off under reduced pressure. To the residue was added ethyl acetate, and the organic layer was carefully washed with saturated aqueous sodium hydrogencarbonate solution and then with saturated aqueous sodium chloride solution, and dried over magnesium sulfate and concentrated under reduced pressure. The resulting crystal was washed with a small amount of diethyl ether to obtain 1.87 g (6.07 mM) of the intended product having a melting point of 201°–204° C., at a yield of 67%.

3-4. Production of N-(2-methyl-3-chlorophenyl)-6-phenylthio-2,3-pyridinedicarboxyimide

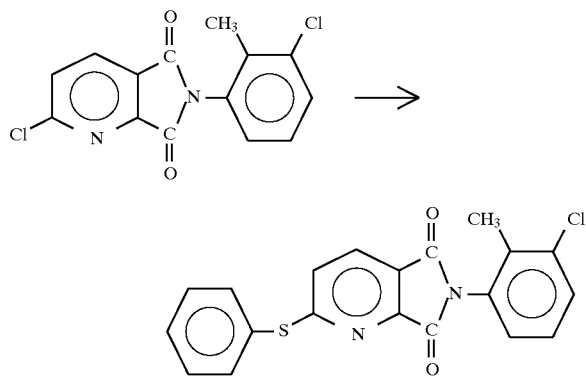

0.32g (2.9 mM) of thiophenol was dissolved in 10 ml of dimethylformamide and to the solution was added 0.12 g (2.9 mM) of sodium hydride (62%). After generation of hydrogen was not seen, the solution was slowly added, at 0° C., to a solution of 0.90 g (2.92 mM) of N-(2-methyl-3-chlorophenyl)-6-chloro-2,3-pyridinedicarboxyimide in 5 ml of dimethylformamide and the reaction was carried out for 1 hour. After disappearance of the starting compound was confirmed, water was added to stop the reaction.

The intended product was extracted with ethyl acetate from the reaction mixture. It was washed with saturated aqueous sodium chloride solution and dried over anhydrous magnesium sulfate. Then, the solvent was distilled off under reduced pressure, and the resulting residue was washed with a small amount of ether to obtain 0.92 g of the intended product having a melting point of 257°–258° C., at a yield of 83%.

3-5. Production of 3-(2-methyl-3-chlorophenyl)-aminocarbonyl-6-phenylthio-2-pyridinecarboxylic acid n-propylamide (compound No. 185)

0.35 g (0.92 mM) of N-(2-methyl-3-chlorophenyl)-6-phenylthio-2,3-pyridinedicarboxyimide was dissolved in 10 ml of dioxane. To the solution was added 90 mg (1.4 mM) of n-propylamine and the reaction was carried out at room temperature for 12 hours.

After completion of the reaction, the reaction mixture was subjected to vacuum distillation and the resulting residue was purified by a silica gel column chromatography using ethyl acetate/n-hexane/chloroform as an eluent to obtain 0.33 g of the intended product as a white crystal having a melting point of 152.5°–153.0° C., at a yield of 82%.

Typical formulation examples and test examples of the present invention are shown below. The present invention is not restricted to these examples.

In the formulation examples, parts are by weight.

Formulation Example 1

| | |
|---|---|
| Present compound | 50 parts |
| Xylene | 40 parts |
| Mixture of polyoxyethylene nonylphenyl ether and calcium alkylbenzenesulfonate | 10 parts |

The above ingredients are uniformly mixed to obtain an emulsifiable concentrate.

Formulation Example 2

| | |
|---|---|
| Present compound | 3 parts |
| Clay powder | 82 parts |
| Diatomaceous earth powder | 15 parts |

The above ingredients are uniformly mixed and ground to obtain a dust.

Formulation Example 3

| | |
|---|---|
| Present compound | 5 parts |
| Mixed powder of bentonite and clay | 90 parts |
| Calcium ligninsulfonate | 5 parts |

The above ingredients are uniformly mixed; the mixture is kneaded with an appropriate amount of water; the kneaded product is granulated and dried to obtain granules.

Formulation Example 4

| | |
|---|---|
| Present compound | 20 parts |
| Kaolin and highly dispersed synthetic silicic acid | 75 parts |

-continued

| | |
|---|---|
| Mixture of polyoxyethylene nonylphenyl ether and calcium alkylbenzenesulfonate | 5 parts |

The above ingredients are uniformly mixed and ground to obtain a wettable powder.

Test Example 1

Herbicidal effect on paddy field weeds of pre-emergence stage

Pots (1/10,000-are) were filled with soil to simulate a paddy field and then planted with seeds of barnyard grass (*Echinochloa crus-galli Beauv.*) and bulrush (*Scirpus juncoides Roxb.* var. *hotarui ohwi*) in the state of pre-emergence. Then, each pot was treated with a herbicide containing, as the active ingredient, one of the present compound shown in Table 1.

After 21 days from the treatment, the herbicidal effect was examined and, by comparing with the result of an untreated pot, the weed control (%) of the herbicide used was calculated. Using this weed control, the herbicidal activity of the herbicide used was rated according to the following criterion.

| Criterion for rating herbicidal activity | |
|---|---|
| Degree of herbicidal activity | Weed control (%) |
| 5 | 100 |
| 4 | 90–99 |
| 3 | 70–89 |
| 2 | 40–69 |
| 1 | 1–39 |
| 0 | 0 |

The results are shown in Table 2.

Test Example 2

Herbicidal effect on paddy field weeds of post-emergence stage

Pots (1/10,000-are) were filled with soil to simulate a paddy field and then planted with seeds of barnyard grass (*Echinochloa crus-qalli Beauv.*), bulrush (*Scirpus juncoides Roxb.* var. *hotarui ohwi*) and pickerelweed (*Monochoria vaginalis* var. *plantaginea Solms-Laub.*). The seeds were grown so as to each produce one-year leaf.

Then, each pot was treated with a herbicide containing, as the active ingredient, one of the present compound shown in Table 1.

After 21 days from the treatment, the herbicidal effect was examined and rated according to the criterion of Example 1.

Simultaneously, the phytotoxicity to rice by each herbicide was also examined and rated according to the following criterion.

Criterion for rating phytotoxicity

| Criterion for rating phytotoxicity | |
|---|---|
| Degree of phytotoxicity | Death of rice plant (%) |
| 5 | 100 |
| 4 | 90–99 |
| 3 | 70–89 |
| 2 | 40–69 |
| 1 | 21–39 |
| 0 | 0–20 (no phytotoxicity) |

The results are shown in Table 2.

TABLE 2

(In Table 2, "—" means "untreated".)

| | | Pre-emergence treatment | | Post-emergence treatment | | | Phytotoxicity |
|---|---|---|---|---|---|---|---|
| No. | Dosage kg/ha | Barnyard grass | Bulrush | Barnyard grass | Bulrush | Pickerelweed | to padding rice plant |
| 1 | 5 | 5 | 5 | 4 | 2 | — | 1 |
| 2 | 5 | 5 | 2 | 3 | 0 | — | 0 |
| 10 | 3 | 5 | 4 | 3 | 3 | 5 | 3 |
| 11 | 3 | 5 | 5 | 5 | 5 | 5 | 5 |
| 12 | 3 | 1 | 4 | 2 | 1 | 0 | 2 |
| 13 | 3 | 5 | 5 | 4 | 4 | 4 | 4 |
| 14 | 3 | 5 | 5 | 5 | 5 | 5 | 5 |
| 15 | 3 | 5 | 5 | 5 | 5 | 5 | 5 |
| 16 | 3 | 3 | 5 | 3 | 2 | 3 | 3 |
| 17 | 3 | 5 | 5 | 4 | 5 | 5 | 4 |
| 19 | 3 | 5 | 4 | 4 | 4 | 5 | 4 |
| 20 | 3 | 5 | 4 | 3 | 3 | 5 | 3 |
| 21 | 3 | 5 | 5 | 4 | 5 | 5 | 4 |
| 22 | 3 | 5 | 5 | 5 | 5 | 5 | 5 |
| 23 | 3 | 5 | 5 | 3 | 4 | 5 | 4 |
| 24 | 3 | 5 | 5 | 5 | 5 | 5 | 5 |
| 25 | 3 | 5 | 5 | 4 | 4 | 5 | 4 |
| 26 | 3 | 4 | 3 | 2 | 2 | 2 | 1 |
| 27 | 3 | 4 | 1 | 0 | 1 | 2 | 0 |
| 28 | 3 | 5 | 5 | 5 | 5 | 5 | 5 |
| 29 | 3 | 5 | 5 | 4 | 4 | 4 | 4 |
| 30 | 3 | 4 | 3 | 4 | 4 | 5 | 3 |
| 31 | 3 | 5 | 5 | 4 | 5 | 5 | 5 |

TABLE 2-continued (In Table 2, "—" means "untreated".)

| | | Pre-emergence treatment | | Post-emergence treatment | | | Phytotoxicity |
|---|---|---|---|---|---|---|---|
| No. | Dosage kg/ha | Barnyard grass | Bulrush | Barnyard grass | Bulrush | Pickerelweed | to padding rice plant |
| 32 | 3 | 5 | 4 | 4 | 3 | 5 | 4 |
| 33 | 3 | 5 | 5 | 5 | 5 | 5 | 5 |
| 34 | 3 | 5 | 3 | 3 | 3 | 5 | 3 |
| 35 | 3 | 5 | 5 | 5 | 4 | 5 | 5 |
| 36 | 3 | 5 | 5 | 4 | 4 | 5 | 5 |
| 37 | 3 | 5 | 4 | 3 | 3 | 5 | 4 |
| 38 | 3 | 3 | 2 | 2 | 1 | 2 | 2 |
| 40 | 3 | 3 | 2 | 4 | 3 | 4 | 4 |
| 43 | 3 | 5 | 5 | 5 | 5 | 5 | 5 |
| 45 | 3 | 2 | 3 | 2 | 2 | 3 | 2 |
| 55 | 5 | 4 | 1 | 3 | 1 | — | 1 |
| 56 | 5 | 5 | 5 | 5 | 5 | — | 3 |
| 57 | 5 | 5 | 4 | 4 | 3 | — | 2 |
| 58 | 5 | 5 | 5 | 5 | 2 | — | 1 |
| 59 | 5 | 5 | 5 | 5 | 5 | — | 4 |
| 60 | 5 | 3 | 0 | 0 | 0 | — | 0 |
| 61 | 5 | 5 | 4 | 5 | 3 | — | 3 |
| 62 | 5 | 5 | 5 | 4 | 4 | — | 2 |
| 63 | 5 | 3 | 0 | 0 | 0 | — | 0 |
| 64 | 5 | 5 | 4 | 4 | 3 | — | 1 |
| 67 | 5 | 5 | 4 | 5 | 3 | — | 2 |
| 68 | 5 | 5 | 3 | 3 | 2 | — | 2 |
| 69 | 5 | 5 | 5 | 5 | 4 | — | 3 |
| 70 | 5 | 4 | 3 | 2 | 0 | — | 2 |
| 72 | 5 | 5 | 4 | 3 | 2 | — | 2 |
| 73 | 5 | 4 | 2 | 3 | 3 | — | 2 |
| 74 | 5 | 5 | 5 | 5 | 4 | — | 3 |
| 75 | 5 | 5 | 5 | 5 | 5 | — | 3 |
| 76 | 5 | 4 | 4 | 2 | 3 | — | 0 |
| 77 | 5 | 5 | 4 | 5 | 4 | — | 3 |
| 79 | 5 | 5 | 5 | 3 | 3 | — | 2 |
| 81 | 5 | 5 | 5 | 4 | 4 | — | 3 |
| 88 | 5 | 5 | 5 | 5 | 5 | — | 2 |
| 89 | 5 | 5 | 5 | 4 | 2 | — | 3 |
| 90 | 5 | 5 | 5 | 4 | 3 | — | 3 |
| 91 | 3 | 5 | 2 | 2 | 2 | 4 | 2 |
| 92 | 3 | 5 | 3 | 2 | 3 | 5 | 2 |
| 93 | 3 | 5 | 5 | 5 | 5 | 5 | 4 |
| 94 | 3 | 5 | 5 | 4 | 4 | 5 | 4 |
| 95 | 3 | 5 | 5 | 5 | 5 | 5 | 5 |
| 96 | 3 | 5 | 5 | 5 | 5 | 5 | 5 |
| 97 | 3 | 5 | 5 | 4 | 4 | 5 | 4 |
| 98 | 3 | 5 | 5 | 5 | 5 | 5 | 5 |
| 99 | 3 | 5 | 5 | 5 | 5 | — | 5 |
| 100 | 3 | 5 | 5 | 5 | 5 | 5 | 5 |
| 101 | 3 | 5 | 5 | 5 | 5 | 5 | 5 |
| 102 | 3 | 5 | 5 | 5 | 5 | 5 | 5 |
| 103 | 3 | 5 | 5 | 5 | 5 | 5 | 5 |
| 104 | 3 | 5 | 5 | 5 | 5 | 5 | 5 |
| 105 | 3 | 5 | 5 | 5 | 5 | 5 | 4 |
| 106 | 3 | 5 | 5 | 4 | 5 | 5 | 4 |
| 107 | 3 | 5 | 5 | 5 | 5 | 5 | 4 |
| 108 | 3 | 5 | 5 | 5 | 5 | 5 | 5 |
| 109 | 3 | 5 | 5 | 5 | 5 | 5 | 4 |
| 110 | 3 | 5 | 5 | 5 | 5 | 5 | 5 |
| 111 | 3 | 5 | 5 | 5 | 5 | 5 | 5 |
| 112 | 3 | 5 | 5 | 5 | 5 | 5 | 5 |
| 113 | 3 | 5 | 5 | 5 | 5 | 5 | 5 |
| 114 | 3 | 5 | 5 | 5 | 5 | 5 | 5 |
| 115 | 3 | 5 | 5 | 4 | 5 | 5 | 4 |
| 116 | 0.3 | 5 | 4 | 3 | 4 | 5 | 3 |
| 117 | 3 | 5 | 5 | 5 | 5 | 5 | 5 |
| 118 | 3 | 5 | 5 | 5 | 5 | 5 | 5 |
| 119 | 3 | 5 | 5 | 5 | 5 | 5 | 5 |
| 120 | 3 | 5 | 5 | 5 | 5 | 5 | 5 |
| 121 | 0.3 | 5 | 4 | 4 | 3 | 4 | 3 |
| 122 | 3 | 5 | 4 | 4 | 5 | 5 | 5 |
| 123 | 3 | 5 | 5 | 5 | 5 | 5 | 5 |
| 124 | 3 | 5 | 5 | 5 | 5 | 5 | 5 |
| 125 | 3 | 5 | 5 | 5 | 5 | 5 | 5 |
| 126 | 3 | 5 | 5 | 5 | 5 | 5 | 5 |

TABLE 2-continued (In Table 2, "—" means "untreated".)

| | | Pre-emergence treatment | | Post-emergence treatment | | | Phytotoxicity |
|---|---|---|---|---|---|---|---|
| No. | Dosage kg/ha | Barnyard grass | Bulrush | Barnyard grass | Bulrush | Pickerelweed | to padding rice plant |
| 127 | 3 | 5 | 5 | 5 | 5 | 5 | 5 |
| 128 | 3 | 5 | 5 | 5 | 5 | 5 | 5 |
| 129 | 3 | 5 | 5 | 5 | 4 | 5 | 5 |
| 130 | 3 | 5 | 5 | 5 | 5 | 5 | 5 |
| 131 | 3 | 5 | 5 | 5 | 5 | 5 | 4 |
| 132 | 3 | 5 | 5 | 5 | 5 | 5 | 4 |
| 133 | 3 | 5 | 5 | 5 | 5 | 5 | 5 |
| 134 | 3 | 5 | 5 | 5 | 5 | 5 | 5 |
| 135 | 3 | 5 | 4 | 4 | 3 | 5 | 4 |
| 136 | 3 | 5 | 4 | 4 | 4 | 4 | 4 |
| 137 | 3 | 5 | 5 | 4 | 4 | 4 | 4 |
| 138 | 5 | 5 | 4 | 5 | 2 | — | 3 |
| 139 | 5 | 5 | 5 | 5 | 3 | — | 3 |
| 140 | 5 | 5 | 5 | 4 | 2 | — | 3 |
| 141 | 3 | 5 | 5 | 5 | 5 | — | 3 |
| 142 | 5 | 5 | 5 | 5 | 4 | — | 2 |
| 143 | 5 | 5 | 5 | 3 | 1 | — | 1 |
| 144 | 5 | 5 | 5 | 5 | 5 | — | 4 |
| 145 | 5 | 5 | 5 | 5 | 5 | — | 4 |
| 146 | 5 | 5 | 5 | 5 | 3 | — | 4 |
| 147 | 5 | 5 | 5 | 5 | 3 | — | 3 |
| 148 | 5 | 5 | 5 | 5 | 4 | — | 4 |
| 149 | 5 | 5 | 5 | 5 | 4 | — | 4 |
| 150 | 5 | 5 | 5 | 5 | 5 | — | 5 |
| 151 | 3 | 5 | 5 | 5 | 4 | 4 | 5 |
| 152 | 3 | 5 | 4 | 4 | 4 | 4 | 4 |
| 153 | 3 | 4 | 4 | 4 | 3 | 4 | 4 |
| 154 | 3 | 5 | 5 | 4 | 4 | 4 | 4 |
| 155 | 3 | 5 | 4 | 4 | 4 | 4 | 4 |
| 156 | 3 | 4 | 3 | 3 | 3 | 3 | 3 |
| 157 | 3 | 5 | 5 | 4 | 4 | 4 | 4 |
| 158 | 3 | 4 | 4 | 3 | 3 | 4 | 4 |
| 159 | 3 | 4 | 5 | 4 | 4 | 4 | 4 |
| 160 | 3 | 4 | 5 | 4 | 4 | 4 | 4 |
| 161 | 3 | 5 | 5 | 4 | 4 | 4 | 4 |
| 162 | 3 | 5 | 5 | 5 | 4 | 5 | 4 |
| 163 | 5 | 5 | 3 | 3 | 3 | — | 3 |
| 164 | 3 | 5 | 4 | 3 | 1 | — | 3 |
| 165 | 3 | 5 | 5 | 5 | 5 | 5 | 5 |
| 166 | 3 | 5 | 5 | 5 | 5 | 5 | 3 |
| 167 | 3 | 5 | 5 | 5 | 5 | 5 | 5 |
| 168 | 3 | 5 | 5 | 5 | 5 | 5 | 5 |
| 169 | 3 | 5 | 5 | 5 | 5 | 5 | 5 |
| 170 | 3 | 5 | 5 | 5 | 5 | 5 | 5 |
| 171 | 3 | 5 | 5 | 5 | 5 | 5 | 5 |
| 172 | 3 | 5 | 5 | 5 | 5 | 5 | 4 |
| 173 | 3 | 5 | 5 | 5 | 5 | 5 | 5 |
| 174 | 3 | 5 | 5 | 5 | 5 | 5 | 5 |
| 175 | 3 | 5 | 5 | 5 | 5 | 5 | 5 |
| 176 | 3 | 5 | 5 | 5 | 5 | 5 | 5 |
| 177 | 3 | 5 | 5 | 4 | 4 | 5 | 4 |
| 178 | 3 | 5 | 5 | 4 | 5 | 5 | 4 |
| 179 | 3 | 5 | 5 | 4 | 4 | 5 | 3 |
| 180 | 3 | 5 | 3 | 3 | 3 | 4 | 3 |
| 181 | 3 | 5 | 3 | 2 | 3 | 4 | 3 |
| 182 | 3 | 5 | 3 | 2 | 4 | 4 | 3 |
| 183 | 3 | 3 | 2 | 0 | 2 | 2 | 0 |
| 184 | 3 | 2 | 4 | 0 | 1 | 1 | 1 |
| 185 | 3 | 5 | 3 | 2 | 2 | 4 | 1 |
| 186 | 3 | 5 | 3 | 1 | 2 | 2 | 1 |
| 187 | 3 | 5 | 2 | 0 | 1 | 3 | 0 |
| 188 | 3 | 5 | 5 | 5 | 5 | 5 | 5 |
| 189 | 3 | 5 | 3 | 3 | 4 | 5 | 3 |
| 190 | 3 | 5 | 5 | 4 | 5 | 5 | 4 |
| 191 | 3 | 5 | 4 | 3 | 4 | 5 | 3 |
| 192 | 5 | 5 | 5 | 1 | 0 | — | 2 |
| 193 | 5 | 4 | 1 | 0 | 0 | — | 2 |
| 194 | 5 | 5 | 4 | 3 | 1 | — | 3 |
| 195 | 5 | 5 | 3 | 3 | 1 | — | 4 |
| 196 | 3 | 5 | 5 | 4 | 5 | 5 | 4 |
| 197 | 3 | 5 | 5 | 5 | 5 | 5 | 4 |

TABLE 2-continued (In Table 2, "—" means "untreated".)

| No. | Dosage kg/ha | Pre-emergence treatment Barnyard grass | Bulrush | Post-emergence treatment Barnyard grass | Bulrush | Pickerelweed | Phytotoxicity to padding rice plant |
|---|---|---|---|---|---|---|---|
| 198 | 3 | 5 | 5 | 5 | 5 | 5 | 4 |
| 199 | 3 | 5 | 5 | 5 | 5 | 5 | 5 |
| 200 | 3 | 5 | 5 | 5 | 5 | 5 | 5 |
| 201 | 3 | 5 | 5 | 5 | 5 | 5 | 5 |
| 202 | 3 | 5 | 3 | 3 | 3 | 4 | 3 |
| 203 | 3 | 5 | 4 | 3 | 3 | 4 | 3 |
| 206 | 3 | 5 | 5 | 3 | 2 | 3 | 3 |
| 207 | 3 | 2 | 1 | 1 | 1 | 3 | 3 |
| 210 | 3 | 5 | 5 | 5 | 5 | 5 | 5 |
| 211 | 3 | 5 | 4 | 3 | 3 | 5 | 2 |
| 212 | 3 | 5 | 5 | 5 | 5 | 5 | 4 |
| 213 | 3 | 5 | 5 | 5 | 4 | 5 | 5 |
| 214 | 3 | 5 | 5 | 4 | 4 | 5 | 4 |
| 215 | 3 | 5 | 5 | 4 | 4 | 5 | 4 |
| 216 | 3 | 5 | 5 | 4 | 4 | 5 | 4 |
| 217 | 3 | 5 | 5 | 4 | 4 | 5 | 3 |
| 218 | 3 | 5 | 5 | 5 | 5 | 5 | 5 |
| 219 | 3 | 5 | 5 | 5 | 4 | 5 | 5 |
| 220 | 3 | 5 | 4 | 3 | 2 | 4 | 2 |
| 221 | 3 | 5 | 5 | 4 | 3 | 5 | 3 |
| 224 | 3 | 5 | 5 | 4 | 3 | 5 | 4 |
| 225 | 3 | 5 | 5 | 4 | 4 | 5 | 3 |
| 228 | 3 | 5 | 5 | 5 | 5 | 5 | 5 |
| 229 | 3 | 5 | 5 | 5 | 5 | 5 | 5 |
| 230 | 3 | 5 | 5 | 4 | 5 | 5 | 4 |
| 231 | 3 | 5 | 5 | 5 | 5 | 5 | 5 |
| 232 | 3 | 5 | 5 | 5 | 5 | 5 | 4 |
| 233 | 3 | 5 | 5 | 4 | 5 | 5 | 4 |
| 234 | 3 | 5 | 5 | 3 | 2 | 5 | 3 |
| 235 | 3 | 5 | 5 | 5 | 5 | 5 | 5 |
| 236 | 3 | 5 | 5 | 4 | 5 | 5 | 4 |
| 237 | 3 | 5 | 5 | 2 | 4 | 5 | 2 |
| 238 | 3 | 5 | 5 | 4 | 5 | 5 | 4 |
| 239 | 3 | 5 | 5 | 4 | 5 | 5 | 4 |
| 240 | 3 | 5 | 5 | 4 | 4 | 5 | 3 |
| 241 | 3 | 5 | 5 | 4 | 4 | 5 | 3 |
| 242 | 3 | 4 | 5 | 4 | 4 | 5 | 3 |
| 243 | 3 | 5 | 5 | 5 | 5 | 5 | 5 |
| 244 | 3 | 5 | 5 | 4 | 5 | 5 | 4 |
| 245 | 3 | 5 | 5 | 2 | 3 | 5 | 5 |
| 246 | 3 | 5 | 5 | 4 | 4 | 5 | 4 |
| 247 | 3 | 5 | 5 | 5 | 5 | 5 | 5 |
| 248 | 3 | 5 | 5 | 4 | 5 | 5 | 4 |
| 249 | 3 | 5 | 5 | 5 | 5 | 5 | 5 |
| 250 | 3 | 5 | 5 | 5 | 5 | 5 | 4 |

Test Example 3

Herbicidal effect on upland field weeds of pre-emergence stage

Polyethylene vats of 10 cm×20 cm×5 cm were filled with soil and seeded with foxtail grass (Am), barnyard grass (Ec), velvetleaf (At), cocklebur (Xs), cleavers (Ga), bird's eye speedwell (Vp) (these are injurious weeds of upland fields) and also with wheat (Wh) and soybean (So) both as crops of upland fields. Then, the seeds were covered with soil.

Each vat was treated with a herbicide containing, as the active ingredient, one of the present compounds shown in Table 1, by spraying.

After 14 days from the treatment, the herbicidal effect of the herbicide was examined and the weed control (%) was calculated and the herbicidal activity was rated, both in the same manner as in Test Example 1.

Simultaneously, the phytotoxicity to soybean and wheat by each herbicide was also examined and rated in the same manner as in Test Example 2.

The results are shown in Table 3.

TABLE 3

| No. | Dosage kg/ha | Wh | So | Am | Ec | At | Xs | Ga | Vp |
|---|---|---|---|---|---|---|---|---|---|
| 1 | 5 | 0 | 0 | 1 | 4 | 5 | 0 | 0 | 0 |
| 2 | 5 | 0 | 0 | 1 | 3 | 3 | 0 | 0 | 0 |
| 5 | 5 | 1 | 0 | 0 | 1 | 0 | 0 | 1 | 5 |
| 7 | 5 | 1 | 0 | 1 | 1 | 2 | 0 | 1 | 3 |
| 11 | 3 | 0 | 0 | 1 | 1 | 5 | 1 | 1 | 5 |
| 13 | 3 | 1 | 2 | 1 | 2 | 5 | 1 | 2 | 5 |
| 14 | 3 | 0 | 0 | 0 | 1 | 0 | 0 | 0 | 4 |
| 15 | 3 | 0 | 1 | 1 | 1 | 0 | 0 | 0 | 5 |
| 18 | 3 | 0 | 0 | 0 | 0 | 0 | 0 | 0 | 4 |
| 21 | 3 | 0 | 0 | 1 | 0 | 3 | 2 | 0 | 0 |
| 23 | 3 | 0 | 0 | 0 | 0 | 1 | 0 | 0 | 4 |
| 24 | 3 | 0 | 0 | 1 | 1 | 3 | 1 | 0 | 5 |
| 25 | 3 | 0 | 0 | 1 | 1 | 3 | 1 | 0 | 3 |
| 28 | 3 | 2 | 2 | 3 | 2 | 5 | 5 | 5 | 5 |
| 29 | 3 | 1 | 0 | 1 | 1 | 5 | 0 | 4 | 5 |

TABLE 3-continued

| No. | Dosage kg/ha | Wh | So | Am | Ec | At | Xs | Ga | Vp |
|---|---|---|---|---|---|---|---|---|---|
| 31 | 3 | 2 | 0 | 2 | 2 | 5 | 2 | 3 | 5 |
| 32 | 3 | 0 | 0 | 0 | 1 | 1 | 0 | 0 | 4 |
| 33 | 3 | 3 | 4 | 1 | 5 | 5 | 2 | 4 | 5 |
| 35 | 3 | 0 | 0 | 0 | 1 | 3 | 0 | 3 | 5 |
| 38 | 3 | 0 | 0 | 0 | 0 | 0 | 0 | 0 | 4 |
| 40 | 3 | 0 | 0 | 0 | 0 | 0 | 0 | 0 | 4 |
| 42 | 3 | 0 | 0 | 0 | 2 | 3 | 1 | 0 | 0 |
| 54 | 5 | 1 | 0 | 1 | 1 | 4 | 1 | 0 | 2 |
| 55 | 5 | 1 | 0 | 1 | 2 | 1 | 3 | 1 | 2 |
| 56 | 5 | 1 | 1 | 3 | 5 | 5 | 5 | 4 | 5 |
| 57 | 5 | 1 | 1 | 3 | 4 | 5 | 5 | 3 | 5 |
| 58 | 5 | 2 | 0 | 1 | 4 | 3 | 3 | 3 | 4 |
| 61 | 5 | 1 | 1 | 1 | 4 | 4 | 3 | 3 | 4 |
| 62 | 5 | 3 | 3 | 3 | 5 | 5 | 4 | 5 | 5 |
| 63 | 5 | 0 | 1 | 2 | 1 | 2 | 1 | 0 | 5 |
| 64 | 5 | 1 | 0 | 1 | 2 | 2 | 2 | 1 | 3 |
| 67 | 5 | 1 | 1 | 2 | 2 | 4 | 2 | 2 | 3 |
| 69 | 5 | 1 | 1 | 4 | 4 | 5 | 3 | 2 | 5 |
| 70 | 5 | 1 | 1 | 3 | 5 | 5 | 0 | 4 | 5 |
| 71 | 5 | 1 | 1 | 1 | 1 | 4 | 0 | 2 | 5 |
| 72 | 5 | 1 | 3 | 1 | 2 | 5 | 1 | 5 | 5 |
| 75 | 5 | 3 | 4 | 4 | 5 | 5 | 5 | 5 | 5 |
| 76 | 5 | 0 | 3 | 1 | 2 | 4 | 3 | 1 | 4 |
| 77 | 5 | 1 | 0 | 1 | 1 | 2 | 2 | 4 | 3 |
| 78 | 5 | 0 | 0 | 0 | 1 | 1 | 4 | 0 | 1 |
| 79 | 5 | 2 | 2 | 4 | 5 | 5 | 5 | 5 | 5 |
| 81 | 5 | 2 | 2 | 4 | 5 | 5 | 5 | 5 | 5 |
| 88 | 5 | 1 | 1 | 1 | 4 | 3 | 2 | 2 | 3 |
| 89 | 3 | 1 | 1 | 1 | 4 | 3 | 2 | 3 | 3 |
| 90 | 5 | 1 | 0 | 1 | 4 | 3 | 3 | 3 | 5 |
| 93 | 3 | 0 | 0 | 5 | 0 | 5 | 1 | 0 | 5 |
| 96 | 3 | 0 | 0 | 0 | 0 | 5 | 0 | 3 | 3 |
| 98 | 3 | 1 | 0 | 3 | 1 | 5 | 1 | 2 | 5 |
| 99 | 5 | 2 | 4 | 3 | 4 | 5 | 5 | 4 | 5 |
| 100 | 1 | 5 | 5 | 5 | 5 | 5 | 5 | 5 | 5 |
| 101 | 3 | 4 | 5 | 5 | 5 | 5 | 5 | 5 | 5 |
| 102 | 1 | 5 | 5 | 5 | 5 | 5 | 5 | 5 | 5 |
| 103 | 3 | 2 | 0 | 5 | 5 | 5 | 4 | 3 | 5 |
| 104 | 3 | 4 | 3 | 5 | 5 | 5 | 3 | 5 | 5 |
| 105 | 3 | 0 | 0 | 2 | 3 | 2 | 2 | 1 | 5 |
| 106 | 3 | 2 | 1 | 5 | 5 | 5 | 3 | 5 | 5 |
| 107 | 3 | 2 | 0 | 5 | 5 | 5 | 5 | 2 | 5 |
| 108 | 3 | 4 | 2 | 5 | 5 | 5 | 2 | 5 | 5 |
| 109 | 3 | 4 | 2 | 5 | 4 | 5 | 2 | 5 | 0 |
| 110 | 3 | 3 | 1 | 5 | 5 | 5 | 5 | 5 | 5 |
| 111 | 3 | 1 | 1 | 2 | 5 | 5 | 2 | 3 | 5 |
| 112 | 3 | 4 | 5 | 5 | 5 | 5 | 5 | 5 | 5 |
| 113 | 3 | 5 | 3 | 5 | 5 | 5 | 5 | 5 | 5 |
| 114 | 1 | 4 | 5 | 5 | 5 | 5 | 5 | 5 | 5 |
| 115 | 1 | 3 | 3 | 2 | 5 | 5 | 1 | 5 | 5 |
| 117 | 1 | 5 | 5 | 5 | 5 | 5 | 5 | 5 | 5 |
| 118 | 3 | 1 | 0 | 5 | 5 | 5 | 3 | 5 | 5 |
| 119 | 3 | 0 | 0 | 5 | 5 | 5 | 5 | 5 | 5 |
| 120 | 1 | 4 | 3 | 5 | 5 | 5 | 5 | 5 | 5 |
| 122 | 1 | 1 | 0 | 1 | 1 | 5 | 0 | 3 | 5 |
| 123 | 1 | 4 | 2 | 5 | 5 | 5 | 4 | 5 | 5 |
| 124 | 1 | 3 | 3 | 5 | 5 | 5 | 5 | 4 | 5 |
| 125 | 1 | 3 | 0 | 5 | 5 | 5 | 4 | 4 | 5 |
| 126 | 1 | 4 | 3 | 4 | 5 | 5 | 5 | 4 | 5 |
| 127 | 1 | 4 | 3 | 5 | 5 | 5 | 5 | 5 | 5 |
| 128 | 1 | 3 | 2 | 5 | 5 | 5 | 5 | 5 | 5 |
| 129 | 1 | 3 | 5 | 5 | 5 | 5 | 5 | 5 | 5 |
| 130 | 1 | 3 | 4 | 5 | 5 | 5 | 2 | 5 | 5 |
| 131 | 1 | 4 | 4 | 3 | 5 | 5 | 3 | 4 | 5 |
| 132 | 1 | 4 | 4 | 4 | 5 | 5 | 3 | 4 | 5 |
| 133 | 1 | 4 | 4 | 5 | 5 | 5 | 5 | 5 | 5 |
| 134 | 1 | 5 | 4 | 5 | 5 | 5 | 5 | 5 | 5 |
| 135 | 1 | 2 | 3 | 4 | 4 | 5 | 4 | 3 | 5 |
| 136 | 1 | 2 | 2 | 5 | 4 | 4 | 4 | 4 | 5 |
| 137 | 1 | 2 | 2 | 4 | 4 | 5 | 4 | 3 | 5 |
| 138 | 5 | 1 | 0 | 1 | 2 | 1 | 3 | 1 | 4 |
| 139 | 5 | 3 | 3 | 4 | 5 | 5 | 5 | 2 | 5 |
| 140 | 5 | 4 | 2 | 5 | 4 | 5 | 5 | 4 | 5 |
| 141 | 5 | 2 | 1 | 4 | 5 | 4 | 3 | 4 | 4 |
| 142 | 5 | 4 | 3 | 3 | 5 | 4 | 5 | 4 | 5 |
| 143 | 5 | 3 | 2 | 2 | 4 | 4 | 5 | 3 | 5 |
| 144 | 5 | 4 | 2 | 5 | 5 | 5 | 5 | 4 | 5 |
| 145 | 5 | 4 | 3 | 4 | 5 | 5 | 5 | 4 | 5 |
| 146 | 5 | 1 | 0 | 3 | 4 | 1 | 0 | 0 | 5 |
| 147 | 5 | 3 | 1 | 3 | 4 | 5 | 1 | 1 | 5 |
| 148 | 5 | 2 | 2 | 3 | 4 | 5 | 3 | 3 | 2 |
| 149 | 5 | 1 | 2 | 2 | 4 | 4 | 2 | 1 | 1 |
| 150 | 5 | 3 | 4 | 5 | 4 | 4 | 5 | 5 | 5 |
| 151 | 3 | 5 | 0 | 5 | 3 | 5 | 0 | 5 | 5 |
| 152 | 3 | 0 | 0 | 1 | 1 | 1 | 0 | 1 | 3 |
| 154 | 3 | 1 | 0 | 5 | 0 | 5 | 1 | 5 | 5 |
| 153 | 3 | 0 | 0 | 2 | 1 | 5 | 0 | 0 | 5 |
| 155 | 3 | 0 | 0 | 0 | 3 | 5 | 0 | 0 | 0 |
| 156 | 3 | 0 | 0 | 1 | 0 | 5 | 0 | 0 | 0 |
| 159 | 3 | 2 | 0 | 1 | 1 | 3 | 1 | 0 | 0 |
| 160 | 3 | 0 | 0 | 0 | 5 | 1 | 0 | 0 | 0 |
| 161 | 3 | 1 | 0 | 4 | 5 | 5 | 1 | 5 | 5 |
| 162 | 3 | 2 | 0 | 1 | 1 | 2 | 1 | 2 | 5 |
| 163 | 5 | 1 | 0 | 1 | 4 | 5 | 1 | 3 | 5 |
| 164 | 3 | 1 | 0 | 1 | 1 | 4 | 2 | 5 | 1 |
| 165 | 1 | 4 | 3 | 5 | 5 | 5 | 5 | 4 | 5 |
| 166 | 1 | 3 | 1 | 5 | 5 | 5 | 5 | 4 | 5 |
| 167 | 1 | 5 | 5 | 5 | 5 | 5 | 5 | 5 | 5 |
| 168 | 3 | 2 | 0 | 5 | 4 | 5 | 2 | 5 | 5 |
| 169 | 3 | 5 | 3 | 5 | 5 | 5 | 2 | 5 | 5 |
| 170 | 3 | 3 | 1 | 5 | 5 | 5 | 2 | 5 | 5 |
| 171 | 3 | 4 | 2 | 5 | 5 | 5 | 1 | 3 | 5 |
| 172 | 3 | 5 | 4 | 5 | 5 | 5 | 1 | 3 | 5 |
| 173 | 1 | 5 | 5 | 5 | 5 | 5 | 5 | 5 | 5 |
| 174 | 1 | 4 | 4 | 5 | 5 | 5 | 2 | 4 | 5 |
| 175 | 1 | 3 | 2 | 5 | 5 | 5 | 4 | 5 | 5 |
| 176 | 3 | 3 | 2 | 5 | 5 | 5 | 5 | 4 | 5 |
| 177 | 3 | 1 | 0 | 2 | 2 | 5 | 0 | 4 | 4 |
| 178 | 3 | 3 | 0 | 3 | 3 | 2 | 0 | 5 | 5 |
| 179 | 3 | 3 | 0 | 5 | 3 | 5 | 2 | 5 | 2 |
| 180 | 1 | 1 | 0 | 2 | 3 | 5 | 1 | 4 | 4 |
| 181 | 1 | 0 | 0 | 1 | 1 | 0 | 0 | 1 | 3 |
| 182 | 1 | 0 | 0 | 1 | 1 | 0 | 1 | 1 | 3 |
| 185 | 3 | 0 | 3 | 0 | 0 | 1 | 1 | 3 | 5 |
| 188 | 5 | 4 | 3 | 5 | 5 | 5 | 5 | 5 | 5 |
| 189 | 5 | 4 | 0 | 1 | 5 | 5 | 2 | 4 | 5 |
| 190 | 5 | 3 | 1 | 4 | 5 | 5 | 2 | 5 | 5 |
| 191 | 5 | 3 | 0 | 1 | 4 | 5 | 0 | 2 | 5 |
| 192 | 5 | 3 | 0 | 2 | 3 | 3 | 0 | 4 | 5 |
| 193 | 5 | 1 | 0 | 1 | 1 | 1 | 1 | 1 | 5 |
| 194 | 5 | 3 | 1 | 4 | 4 | 3 | 2 | 2 | 5 |
| 195 | 5 | 4 | 1 | 4 | 4 | 4 | 2 | 5 | 5 |
| 196 | 5 | 3 | 4 | 5 | 5 | 5 | 3 | 4 | 5 |
| 197 | 5 | 4 | 5 | 5 | 5 | 5 | 5 | 5 | 5 |
| 198 | 5 | 4 | 4 | 5 | 5 | 5 | 4 | 5 | 5 |
| 199 | 5 | 4 | 3 | 5 | 5 | 5 | 5 | 5 | 5 |
| 200 | 5 | 5 | 4 | 5 | 5 | 5 | 5 | 5 | 5 |
| 201 | 5 | 4 | 4 | 5 | 5 | 5 | 5 | 5 | 5 |
| 202 | 1 | 0 | 0 | 1 | 2 | 2 | 0 | 0 | 5 |
| 203 | 1 | 0 | 0 | 2 | 2 | 4 | 0 | 1 | 5 |
| 206 | 3 | 2 | 0 | 3 | 4 | 5 | 3 | 1 | 5 |
| 210 | 1 | 0 | 0 | 4 | 5 | 4 | 0 | 5 | 5 |
| 211 | 1 | 1 | 0 | 3 | 5 | 5 | 0 | 4 | 5 |
| 212 | 1 | 1 | 1 | 1 | 5 | 4 | 4 | 3 | 5 |
| 213 | 1 | 1 | 0 | 2 | 1 | 5 | 3 | 4 | 5 |
| 214 | 1 | 2 | 2 | 1 | 5 | 4 | 3 | 4 | 5 |
| 215 | 1 | 2 | 1 | 5 | 5 | 5 | 4 | 4 | 5 |
| 216 | 1 | 2 | 0 | 2 | 5 | 4 | 1 | 3 | 5 |
| 217 | 1 | 1 | 0 | 3 | 5 | 5 | 1 | 5 | 5 |
| 218 | 1 | 4 | 2 | 5 | 5 | 5 | 4 | 5 | 5 |
| 219 | 1 | 2 | 0 | 5 | 5 | 5 | 0 | 5 | 5 |
| 220 | 1 | 0 | 0 | 5 | 2 | 4 | 0 | 4 | 5 |
| 221 | 1 | 1 | 0 | 5 | 5 | 5 | 0 | 5 | 5 |
| 224 | 1 | 3 | 0 | 0 | 3 | 5 | 0 | 0 | 0 |
| 225 | 1 | 0 | 0 | 0 | 5 | 5 | 0 | 1 | 5 |
| 228 | 5 | 4 | 5 | 5 | 5 | 5 | 5 | 5 | 5 |
| 229 | 3 | 4 | 5 | 5 | 5 | 5 | 4 | 5 | 5 |
| 230 | 5 | 4 | 4 | 5 | 5 | 5 | 5 | 5 | 5 |
| 231 | 5 | 5 | 5 | 5 | 5 | 5 | 5 | 5 | 5 |
| 232 | 1 | 4 | 5 | 5 | 5 | 5 | 5 | 5 | 5 |
| 233 | 1 | 0 | 0 | 5 | 5 | 5 | 5 | 5 | 5 |
| 234 | 1 | 0 | 0 | 1 | 3 | 5 | 0 | 5 | 5 |

TABLE 3-continued

| No. | Dosage kg/ha | Wh | So | Am | Ec | At | Xs | Ga | Vp |
|---|---|---|---|---|---|---|---|---|---|
| 235 | 1 | 0 | 2 | 5 | 5 | 5 | 5 | 5 | 5 |
| 236 | 1 | 3 | 5 | 5 | 5 | 5 | 5 | 5 | 5 |
| 237 | 1 | 2 | 4 | 4 | 4 | 5 | 3 | 5 | 5 |
| 238 | 1 | 3 | 4 | 5 | 5 | 5 | 5 | 5 | 5 |
| 239 | 1 | 4 | 5 | 5 | 5 | 5 | 3 | 5 | 5 |
| 240 | 1 | 3 | 5 | 5 | 5 | 5 | 5 | 2 | 5 |
| 241 | 1 | 3 | 5 | 5 | 5 | 5 | 2 | 1 | 5 |
| 242 | 1 | 2 | 0 | 5 | 5 | 5 | 2 | 0 | 5 |
| 243 | 5 | 5 | 5 | 5 | 5 | 5 | 5 | 5 | 5 |
| 244 | 5 | 4 | 3 | 5 | 5 | 5 | 4 | 5 | 5 |
| 245 | 1 | 2 | 0 | 2 | 4 | 4 | 0 | 2 | 5 |
| 246 | 1 | 3 | 0 | 5 | 5 | 0 | 0 | 5 | 5 |
| 247 | 1 | 4 | 1 | 5 | 5 | 5 | 5 | 5 | 5 |
| 248 | 1 | 4 | 4 | 5 | 5 | 5 | 5 | 5 | 5 |
| 249 | 1 | 4 | 3 | 5 | 5 | 5 | 4 | 5 | 5 |
| 250 | 1 | 4 | 4 | 5 | 5 | 5 | 4 | 5 | 5 |

Test Example 4

Herbicidal effect on upland field weeds of post-emergence stage

Polyethylene vats of 10 cm×20 cm×5 cm were filled with soil and seeded with various injurious weeds of upland fields shown below and also with wheat (Wh) and soybean (So) both as crops of upland fields. Then, the seeds were covered with soil and grown to the following leaf stages. Each vat was treated with a herbicide containing, as the active ingredient, one of the present compounds shown in Table 1, by spraying.

After 14 days from the treatment, the herbicidal effect of the herbicide was examined and the weed control (%) was calculated and the herbicidal activity was rated, both in the same manner as in Test Example 1. Simultaneously, the phytotoxicity to soybean and wheat by each herbicide was also examined and rated in the same manner as in Test Example 2.

| Weeds tested and their leaf stages, and leaf stages of soybean and wheat | |
|---|---|
| Weed or crop | Leaf stage |
| Foxtail grass (Am) | 1–2 |
| Barnyard grass (Ec) | 1–2 |
| Velvetleaf (At) | 2 |
| Cocklebur (Xs) | 2 |
| Cleavers (Ga) | 1 |
| Bird's eye speedwell (Vp) | Cotyledon - 1 |
| Wheat (Wh) | 2 |
| Soybean (So) | 1 |

The results are shown in Table 4.

| No. | Dosage kg/ha | Wh | So | Am | Ec | At | Xs | Ga | Vp |
|---|---|---|---|---|---|---|---|---|---|
| 9 | 3 | 0 | 0 | 0 | 0 | 0 | 0 | 0 | 5 |
| 10 | 3 | 3 | 1 | 1 | 3 | 5 | 2 | 4 | 5 |
| 11 | 3 | 2 | 2 | 3 | 4 | 5 | 3 | 4 | 5 |
| 12 | 3 | 4 | 3 | 2 | 2 | 5 | 2 | 4 | 5 |
| 13 | 3 | 2 | 2 | 1 | 3 | 3 | 2 | 1 | 5 |
| 14 | 3 | 4 | 2 | 3 | 3 | 4 | 2 | 3 | 5 |
| 15 | 3 | 2 | 2 | 2 | 4 | 5 | 3 | 2 | 5 |
| 16 | 3 | 4 | 2 | 5 | 4 | 5 | 2 | 2 | 5 |
| 17 | 3 | 2 | 2 | 1 | 2 | 5 | 1 | 2 | 5 |
| 19 | 3 | 1 | 2 | 0 | 1 | 2 | 0 | 0 | 5 |
| 21 | 3 | 2 | 2 | 2 | 4 | 4 | 2 | 0 | 5 |
| 22 | 3 | 4 | 3 | 5 | 5 | 5 | 2 | 1 | 5 |
| 23 | 3 | 1 | 1 | 1 | 2 | 2 | 1 | 1 | 4 |
| 24 | 3 | 2 | 1 | 2 | 3 | 3 | 2 | 2 | 5 |
| 25 | 3 | 1 | 2 | 1 | 1 | 3 | 1 | 1 | 4 |
| 28 | 3 | 5 | 3 | 5 | 5 | 5 | 3 | 5 | 5 |
| 29 | 3 | 5 | 3 | 5 | 5 | 4 | 3 | 5 | 5 |
| 30 | 3 | 2 | 0 | 2 | 2 | 5 | 2 | 3 | 5 |
| 31 | 3 | 4 | 1 | 5 | 5 | 5 | 3 | 5 | 5 |
| 32 | 3 | 4 | 2 | 1 | 3 | 5 | 2 | 3 | 5 |
| 33 | 3 | 4 | 3 | 4 | 5 | 5 | 4 | 3 | 5 |
| 34 | 3 | 0 | 0 | 0 | 0 | 4 | 1 | 0 | 5 |
| 35 | 3 | 1 | 2 | 1 | 2 | 5 | 1 | 1 | 5 |
| 36 | 3 | 3 | 2 | 4 | 5 | 5 | 5 | 2 | 5 |
| 37 | 3 | 1 | 2 | 1 | 1 | 2 | 0 | 1 | 5 |
| 38 | 3 | 0 | 0 | 0 | 0 | 0 | 0 | 1 | 5 |
| 39 | 3 | 0 | 0 | 0 | 0 | 0 | 0 | 1 | 5 |
| 40 | 3 | 2 | 0 | 0 | 0 | 0 | 0 | 0 | 5 |
| 41 | 3 | 0 | 0 | 0 | 0 | 5 | 1 | 0 | 5 |
| 42 | 3 | 3 | 1 | 5 | 5 | 5 | 4 | 5 | 5 |
| 49 | 3 | 1 | 1 | 1 | 1 | 5 | 1 | 3 | 5 |
| 50 | 3 | 1 | 0 | 1 | 0 | 4 | 1 | 0 | 5 |
| 52 | 0 | 0 | 0 | 0 | 0 | 1 | 1 | 0 | 4 |
| 56 | 5 | 0 | 1 | 1 | 1 | 3 | 3 | 1 | 2 |
| 58 | 5 | 1 | 2 | 2 | 2 | 3 | 2 | 2 | 2 |
| 62 | 5 | 1 | 2 | 2 | 2 | 4 | 2 | 2 | 3 |
| 69 | 5 | 0 | 2 | 1 | 1 | 3 | 1 | 1 | 3 |
| 70 | 5 | 1 | 1 | 1 | 1 | 3 | 3 | 4 | 5 |
| 72 | 5 | 1 | 1 | 1 | 2 | 4 | 3 | 3 | 5 |
| 75 | 5 | 1 | 3 | 1 | 1 | 4 | 2 | 1 | 3 |
| 76 | 5 | 0 | 2 | 1 | 1 | 3 | 2 | 1 | 3 |
| 77 | 5 | 1 | 3 | 2 | 2 | 3 | 2 | 2 | 3 |
| 79 | 5 | 1 | 1 | 1 | 3 | 5 | 3 | 3 | 5 |
| 81 | 5 | 0 | 1 | 1 | 2 | 5 | 3 | 3 | 5 |
| 88 | 2 | 2 | 2 | 2 | 2 | 2 | 3 | 1 | 1 |
| 89 | 3 | 1 | 2 | 2 | 2 | 1 | 3 | 1 | 2 |
| 91 | 3 | 1 | 0 | 1 | 2 | 3 | 1 | 0 | 1 |
| 92 | 3 | 0 | 0 | 0 | 1 | 5 | 0 | 2 | 4 |
| 93 | 3 | 1 | 0 | 3 | 5 | 5 | 2 | 5 | 5 |
| 94 | 3 | 1 | 0 | 2 | 4 | 5 | 2 | 4 | 5 |
| 95 | 3 | 3 | 0 | 2 | 5 | 5 | 4 | 5 | 5 |
| 96 | 3 | 2 | 0 | 2 | 5 | 5 | 4 | 5 | 5 |
| 97 | 3 | 2 | 0 | 5 | 5 | 5 | 3 | 5 | 5 |
| 98 | 3 | 4 | 2 | 5 | 5 | 5 | 4 | 5 | 5 |
| 99 | 5 | 0 | 2 | 1 | 3 | 3 | 3 | 1 | 1 |
| 100 | 1 | 4 | 3 | 5 | 5 | 5 | 5 | 5 | 5 |
| 101 | 3 | 4 | 4 | 5 | 4 | 5 | 4 | 4 | 5 |
| 102 | 1 | 3 | 3 | 5 | 4 | 5 | 3 | 5 | 5 |
| 103 | 3 | 4 | 2 | 5 | 5 | 5 | 4 | 5 | 5 |
| 104 | 3 | 5 | 4 | 5 | 5 | 5 | 4 | 4 | 5 |
| 105 | 3 | 1 | 1 | 3 | 5 | 5 | 2 | 4 | 5 |
| 106 | 3 | 4 | 3 | 4 | 5 | 5 | 2 | 4 | 5 |
| 107 | 3 | 4 | 2 | 4 | 5 | 5 | 3 | 5 | 5 |
| 108 | 3 | 5 | 3 | 5 | 5 | 5 | 4 | 5 | 5 |
| 109 | 3 | 0 | 2 | 0 | 5 | 5 | 3 | 0 | 0 |
| 110 | 3 | 5 | 1 | 5 | 5 | 5 | 3 | 4 | 5 |
| 111 | 3 | 4 | 3 | 5 | 5 | 5 | 4 | 5 | 5 |
| 112 | 3 | 5 | 3 | 5 | 4 | 3 | 1 | 5 | 5 |
| 113 | 3 | 5 | 4 | 5 | 5 | 5 | 5 | 5 | 5 |
| 114 | 1 | 2 | 2 | 2 | 4 | 5 | 2 | 2 | 5 |
| 115 | 1 | 1 | 0 | 0 | 4 | 4 | 2 | 1 | 2 |
| 116 | 0.3 | 0 | 0 | 0 | 0 | 5 | 0 | 0 | 3 |
| 117 | 1 | 4 | 2 | 4 | 5 | 5 | 4 | 5 | 4 |
| 118 | 3 | 5 | 3 | 5 | 5 | 5 | 5 | 5 | 5 |
| 119 | 3 | 5 | 2 | 5 | 5 | 5 | 5 | 5 | 5 |
| 120 | 1 | 3 | 2 | 2 | 5 | 5 | 2 | 3 | 5 |
| 121 | 0.3 | 0 | 0 | 0 | 0 | 5 | 0 | 0 | 5 |
| 122 | 1 | 1 | 2 | 1 | 4 | 5 | 1 | 1 | 5 |
| 123 | 1 | 4 | 3 | 3 | 5 | 5 | 5 | 5 | 5 |
| 124 | 1 | 4 | 3 | 4 | 5 | 5 | 5 | 5 | 5 |
| 125 | 1 | 3 | 4 | 2 | 5 | 5 | 2 | 4 | 5 |
| 126 | 1 | 3 | 0 | 2 | 4 | 5 | 2 | 5 | 5 |
| 127 | 1 | 2 | 4 | 2 | 5 | 5 | 3 | 3 | 5 |
| 128 | 1 | 1 | 4 | 1 | 4 | 5 | 3 | 1 | 5 |
| 129 | 1 | 2 | 4 | 2 | 5 | 5 | 3 | 4 | 5 |
| 130 | 1 | 3 | 4 | 1 | 5 | 5 | 3 | 4 | 5 |
| 131 | 1 | 3 | 3 | 1 | 5 | 5 | 3 | 2 | 5 |
| 132 | 1 | 3 | 3 | 1 | 4 | 5 | 3 | 2 | 5 |
| 133 | 1 | 4 | 3 | 5 | 4 | 5 | 3 | 4 | 5 |

| No. | Dosage kg/ha | Wh | So | Am | Ec | At | Xs | Ga | Vp |
|---|---|---|---|---|---|---|---|---|---|
| 134 | 1 | 4 | 4 | 5 | 5 | 5 | 4 | 5 | 5 |
| 135 | 1 | 0 | 2 | 1 | 2 | 3 | 1 | 1 | 5 |
| 136 | 1 | 0 | 0 | 1 | 0 | 4 | 1 | 1 | 5 |
| 137 | 1 | 0 | 1 | 1 | 1 | 4 | 1 | 0 | 5 |
| 138 | 5 | 1 | 2 | 0 | 1 | 3 | 2 | 2 | 3 |
| 139 | 5 | 3 | 4 | 3 | 4 | 4 | 3 | 3 | 5 |
| 140 | 5 | 1 | 3 | 2 | 3 | 3 | 3 | 3 | 3 |
| 141 | 5 | 1 | 3 | 1 | 2 | 4 | 3 | 2 | 5 |
| 142 | 5 | 1 | 2 | 2 | 2 | 2 | 3 | 1 | 2 |
| 144 | 5 | 2 | 3 | 2 | 2 | 3 | 2 | 3 | 5 |
| 145 | 5 | 1 | 3 | 2 | 2 | 4 | 4 | 2 | 5 |
| 147 | 5 | 1 | 3 | 2 | 2 | 3 | 3 | 2 | 4 |
| 148 | 5 | 2 | 3 | 2 | 1 | 4 | 3 | 3 | — |
| 150 | 5 | 1 | 3 | 1 | 2 | 2 | 3 | 2 | 3 |
| 151 | 3 | 3 | 0 | 5 | 0 | 0 | 0 | 0 | 5 |
| 152 | 3 | 2 | 1 | 2 | 2 | 5 | 2 | 4 | 5 |
| 153 | 3 | 0 | 0 | 1 | 1 | 5 | 1 | 2 | 3 |
| 154 | 3 | 3 | 0 | 4 | 4 | 5 | 1 | 5 | 5 |
| 155 | 3 | 1 | 0 | 1 | 2 | 5 | 1 | 1 | 5 |
| 156 | 3 | 1 | 0 | 0 | 0 | 5 | 1 | 2 | 0 |
| 157 | 3 | 2 | 0 | 1 | 2 | 5 | 3 | 3 | 2 |
| 158 | 3 | 0 | 0 | 1 | 1 | 5 | 1 | 2 | 2 |
| 159 | 3 | 2 | 0 | 1 | 3 | 5 | 1 | 5 | 5 |
| 160 | 3 | 0 | 1 | 2 | 3 | 5 | 3 | 3 | 5 |
| 161 | 3 | 2 | 1 | 2 | 4 | 5 | 3 | 3 | 5 |
| 162 | 3 | 4 | 0 | 5 | 5 | 5 | 3 | 5 | 5 |
| 165 | 1 | 2 | 1 | 5 | 5 | 5 | 2 | 4 | 5 |
| 166 | 1 | 2 | 0 | 4 | 4 | 5 | 3 | 0 | 5 |
| 167 | 1 | 3 | 1 | 4 | 5 | 5 | 3 | 1 | 5 |
| 168 | 3 | 5 | 4 | 5 | 5 | 5 | 5 | 5 | 5 |
| 169 | 3 | 5 | 4 | 5 | 5 | 5 | 4 | 4 | 5 |
| 170 | 3 | 5 | 4 | 5 | 5 | 5 | 4 | 5 | 5 |
| 171 | 3 | 5 | 4 | 5 | 5 | 5 | 2 | 4 | 3 |
| 172 | 3 | 5 | 4 | 5 | 5 | 5 | 3 | 4 | 5 |
| 173 | 1 | 4 | 2 | 2 | 5 | 5 | 3 | 4 | 5 |
| 174 | 1 | 3 | 1 | 3 | 5 | 5 | 3 | 3 | 5 |
| 175 | 1 | 3 | 1 | 3 | 4 | 5 | 2 | 2 | 2 |
| 176 | 3 | 5 | 3 | 5 | 3 | 5 | 4 | 5 | 5 |
| 177 | 3 | 3 | 2 | 3 | 2 | 5 | 3 | 4 | 5 |
| 178 | 3 | 4 | 2 | 3 | 2 | 5 | 4 | 4 | 5 |
| 179 | 3 | 2 | 3 | 2 | 2 | 5 | 3 | 3 | 5 |
| 180 | 1 | 2 | 0 | 1 | 4 | 5 | 2 | 3 | 5 |
| 181 | 1 | 2 | 0 | 1 | 1 | 4 | 1 | 1 | 1 |
| 182 | 1 | 0 | 0 | 0 | 0 | 5 | 1 | 2 | 0 |
| 185 | 3 | 2 | 0 | 1 | 1 | 5 | 2 | 4 | 4 |
| 186 | 3 | 1 | 1 | 1 | 1 | 4 | 2 | 3 | 1 |
| 187 | 3 | 0 | 0 | 1 | 1 | 5 | 1 | 2 | 0 |
| 188 | 5 | 5 | 1 | 2 | 5 | 5 | 5 | 4 | 5 |
| 190 | 5 | 2 | 2 | 2 | 3 | 5 | 3 | 1 | 5 |
| 196 | 5 | 3 | 2 | 4 | 3 | 5 | 3 | 3 | 4 |
| 197 | 5 | 4 | 3 | 5 | 4 | 5 | 3 | 4 | 5 |
| 198 | 5 | 4 | 3 | 5 | 4 | 5 | 2 | 5 | 5 |
| 199 | 5 | 5 | 4 | 5 | 5 | 5 | 5 | 5 | 5 |
| 200 | 5 | 5 | 4 | 5 | 5 | 5 | 5 | 5 | 5 |
| 201 | 5 | 5 | 4 | 5 | 4 | 5 | 4 | 5 | 5 |
| 210 | 1 | 1 | 4 | 3 | 4 | 5 | 5 | 5 | 5 |
| 211 | 1 | 1 | 0 | 1 | 1 | 4 | 3 | 4 | 5 |
| 212 | 1 | 2 | 1 | 2 | 1 | 3 | 2 | 2 | 4 |
| 213 | 1 | 1 | 1 | 2 | 2 | 3 | 2 | 1 | 5 |
| 214 | 1 | 2 | 1 | 2 | 2 | 5 | 3 | 2 | 5 |
| 215 | 1 | 1 | 1 | 1 | 1 | 4 | 2 | 2 | 1 |
| 218 | 1 | 4 | 4 | 5 | 5 | 5 | 5 | 4 | 5 |
| 219 | 1 | 3 | 1 | 1 | 5 | 5 | 2 | 2 | 3 |
| 220 | 1 | 1 | 1 | 1 | 1 | 5 | 2 | 1 | 2 |
| 221 | 1 | 2 | 1 | 2 | 1 | 5 | 4 | 2 | 4 |
| 224 | 1 | 2 | 1 | 0 | 1 | 4 | 1 | 0 | 1 |
| 225 | 1 | 1 | 0 | 1 | 0 | 5 | 2 | 0 | 1 |
| 228 | 5 | 5 | 4 | 5 | 5 | 5 | 5 | 5 | 5 |
| 229 | 3 | 4 | 4 | 4 | 5 | 5 | 3 | 5 | 5 |
| 230 | 5 | 3 | 4 | 5 | 3 | 5 | 3 | 4 | 5 |
| 231 | 5 | 4 | 4 | 5 | 5 | 5 | 5 | 5 | 5 |
| 232 | 1 | 2 | 2 | 5 | 5 | 5 | 4 | 4 | 5 |
| 233 | 1 | 2 | 0 | 5 | 0 | 5 | 2 | 4 | 5 |
| 234 | 1 | 1 | 0 | 1 | 0 | 5 | 2 | 4 | 3 |
| 235 | 1 | 3 | 5 | 5 | 5 | 5 | 5 | 5 | 5 |
| 236 | 1 | 1 | 0 | 3 | 2 | 3 | 4 | 1 | 4 |
| 238 | 1 | 0 | 0 | 1 | 0 | 4 | 3 | 3 | 5 |
| 239 | 1 | 2 | 0 | 2 | 3 | 3 | 2 | 3 | 4 |
| 240 | 1 | 0 | 0 | 3 | 2 | 5 | 2 | 2 | 1 |
| 241 | 1 | 1 | 1 | 2 | 1 | 2 | 3 | 1 | 2 |
| 243 | 5 | 3 | 1 | 5 | 4 | 5 | 3 | 5 | 5 |
| 244 | 5 | 3 | 1 | 4 | 2 | 5 | 3 | 4 | 5 |
| 246 | 1 | 0 | 0 | 1 | 2 | 5 | 2 | 2 | 2 |
| 247 | 1 | 4 | 0 | 5 | 5 | 5 | 4 | 4 | 5 |
| 248 | 1 | 2 | 1 | 2 | 2 | 5 | 4 | 2 | 5 |
| 249 | 1 | 1 | 2 | 1 | 3 | 3 | 3 | 4 | 5 |
| 250 | 1 | 3 | 2 | 4 | 4 | 3 | 4 | 4 | 4 |

What is claimed is:

1. A pyridine-2,3-dicarboxylic acid diamide derivative represented by the following formula (I):

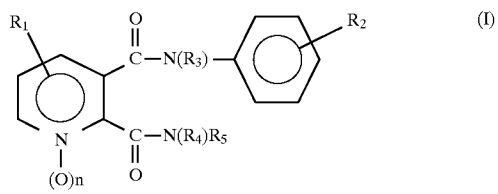

wherein $R^1$ represents one to three substituents which may be the same or different and are selected from the group consisting of a hydrogen atom; a halogen atom; a cyano group; a nitro group; a $(C_{1-6})$ alkyl group; a halo$(C_{1-6})$ alkyl group; a $(C_{1-6})$alkoxy group; a halo $(C_{1-6})$-alkoxy group; a $(C_{1-6})$alkylthio group; a halo $(C_{1-6})$ alkyl-thio group; a $(C_{1-6})$alkylsulfinyl group; a halo$(C_{1-6})$-alkylsulfinyl group; a $(C_{1-6})$alkylsulfonyl group; a halo$(C_{1-6})$alkylsulfonyl group; a $(C_{3-6})$ cycloalkyl group; a $(C_{2-6})$alkenyl group; a $(C_{2-6})$ alkynyl group; a $(C_{1-6})$-alkoxy$(C_{1-6})$alkyl group; a phenyl group; a substituted phenyl group having one or more substituents which may be the same or different and are selected from the group consisting of a halogen atom, a $(C_{1-6})$alkyl group, a halo$(C_{1-6})$ alkyl group, a $(C_{1-6})$ alkoxy group, a halo$(C_{1-6})$-alkoxy group, a $(C_{1-6})$ alkylthio group and a halo$(C_1l_6)$-alkylthio group; a phenoxy group; a substituted phenoxy group having one or more substituents which may be the same or different and are selected from the group consisting of a halogen atom, a $(C_{1-6})$alkyl group, a halo$(C_{1-6})$ alkyl group, a $(C_{1-6})$alkoxy group, a halo$(C_{1-6})$-alkoxy group, a $(C_{1-6})$alkylthio group and a halo$(C_{1-6})$-alkylthio group; a phenylthio group; a substituted phenylthio group having one or more substituents which may be the same or different and are selected from the group consisting of a halogen atom, a $(C_{1-6})$alkyl group, a halo$(C_{1-6})$alkyl group, a $(C_{1-6})$alkoxy group, a halo$(C_{1-6})$alkoxy group, a $(C_{1-6})$alkylthio group and a halo$(C_{1-6})$alkylthio group; and an amino group substituted with a hydrogen atom or a $(C_{1-6})$alkyl group which may be the same or different, $R_2$ represents one to five substituents which may be the same or different and are selected from the group consisting of a hydrogen atom, a halogen atom, a cyano group, a nitro group, a $(C_{1-6})$alkyl group, a halo $(C_{1-6})$ alkyl group, a $(C_{1-6})$alkoxy group, a halo$(C_{1-6})$-alkoxy group, a $(C_{1-6})$alkoxycarbonyl group and a $(C_{1-6})$-alkoxycarbonyl$(C_{1-6})$alkyloxy group, $R_3$ represents a hydrogen atom or a $(C_{1-6})$alkyl group, $R_4$ and $R_5$ may be the same or different and each represent a hydrogen atom; a $(C_{1-6})$alkyl group; a halo$(C_{1-6})$alkyl group; a cyano($C_{1-6}$)alkyl group; a ($C_{3-6}$) cycloalkyl group; a ($C_{3-6}$)cycloalkyl($C_{1-6}$)alkyl group; a ($C_{3-6}$) cycloalkyl($C_{1-6}$)alkyl group having one or more halogen atoms on the ring which may be the same or different; a ($C_{1-6}$)alkoxy($C_{1-6}$)alkyl group; a ($C_{1-6}$) alkylthio($C_{1-6}$)alkyl group; a ($C_{1-6}$)alkoxycarbonyl ($C_{1-6}$) alkyl group; a ($C_{2-6}$)alkenyl group; a ($C_{2-6}$) alkynyl group; an amino group substituted with a hydrogen atom or a ($C_{1-6}$)alkyl group which may be the same or different; an amino($C_{1-6}$)alkyl group substituted with a hydrogen atom or a ($C_{1-6}$)alkyl group which may be the same or different; a phenyl($C_{1-6}$) alkyloxy group; and n represents an integer of 0 or 1.

2. A pyridine-2,3-dicarboxylic acid diamide derivative according to claim 1, wherein in the formula (I), $R_1$ represents one to three substituents which may be the same or different and are selected from the group consisting of a hydrogen atom; a halogen atom; a ($C_{1-6}$)-alkyl group; a halo($C_{1-6}$)alkyl group; a ($C_{1-6}$)alkoxy group; a halo($C_{1-6}$) alkoxy group; a ($C_{1-6}$)alkylthio group; a halo($C_{1-6}$)alkylthio group; a ($C_{1-6}$)alkylsulfonyl group; a halo($C_{1-6}$) alkylsulfonyl group; a ($C_{3-6}$)cycloalkyl group; a phenoxy group; a substituted phenoxy group having one or more substituents which may be the same or different and are selected from the group consisting of a halogen atom, a ($C_{1-6}$)alkyl group, a halo($C_{1-6}$)alkyl group, a ($C_{1-6}$)alkoxy group, a halo($C_1$-$_6$)alkoxy group, a ($C_{1-6}$)-alkylthio group and a halo($C_1$-$_6$) alkylthio group; a phenylthio group; and a substituted phenylthio group having one or more substituents which may be the same or different and are selected from the group consisting of a halogen atom, a ($C_{1-6}$)alkyl group, a halo($C_{1-6}$)alkyl group, a ($C_{1-6}$)alkoxy group, a halo($C_{1-6}$)alkoxy group, a ($C_{1-6}$)alkylthio group and a halo ($C_{1-6}$)alkylthio group, $R_2$ represents one to five substituents which may be the same or different and are selected from the group consisting of a hydrogen atom, a halogen atom, a cyano group, a nitro group, a ($C_{1-6}$)alkyl group, a halo-($C_{1-6}$) alkyl group, a ($C_{1-6}$)alkoxy group and a halo($C_{1-6}$)-alkoxy group, $R_3$ represents a hydrogen atom, $R_4$ and $R_5$ may be the same or different and each represent a hydrogen atom; a ($C_{1-6}$)alkyl group; a halo-($C_{1-6}$) alkyl group; a cyano($C_{1-6}$)alkyl group; a ($C_{3-6}$)cycloalkyl group; a ($C_{3-6}$) cycloalkyl($C_{1-6}$) alkyl group; a ($C_{3-6}$)-cycloalkyl($C_{1-6}$)alkyl group having one or more halogen atoms on the ring which may be the same or different; a ($C_{1-6}$)alkoxy($C_{1-6}$)alkyl group; a($C_{1-6}$) alkylthio($C_{1-6}$) alkyl group; a ($C_{1-6}$)alkoxycarbonyl ($C_{1-6}$) alkyl group; an amino($C_{1-6}$) alkyl group substituted with a hydrogen atom or a ($C_{1-6}$)alkyl group which may be the same or different; a phenyl($C_{1-6}$) alkyloxy group; and n represents an integer of 0 or 1.

3. A herbicidal composition containing, as an active ingredient, the pyridine-2,3-dicarboxylic acid diamide derivative defined in claim 1, and a carrier.

4. A herbicidal composition containing, as an active ingredient, the pyridine-2,3-dicarboxylic acid diamide derivative defined in claim 2, and a carrier.

* * * * *